(12) United States Patent
Marino et al.

(10) Patent No.: US 9,510,955 B2
(45) Date of Patent: Dec. 6, 2016

(54) ARTICULATING INTERBODY CAGE AND METHODS THEREOF

(71) Applicant: Trinity Orthopedics, LLC, San Diego, CA (US)

(72) Inventors: James F. Marino, San Diego, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 0 days.

(21) Appl. No.: 14/402,083

(22) PCT Filed: May 17, 2013

(86) PCT No.: PCT/US2013/041664
§ 371 (c)(1),
(2) Date: Nov. 18, 2014

(87) PCT Pub. No.: WO2013/173767
PCT Pub. Date: Nov. 21, 2013

(65) Prior Publication Data
US 2015/0148908 A1    May 28, 2015

Related U.S. Application Data

(60) Provisional application No. 61/649,029, filed on May 18, 2012, provisional application No. 61/718,143, (Continued)

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30734* (2013.01); *A61F 2/30771* (2013.01); *A61F 2/442* (2013.01);
(Continued)

(58) Field of Classification Search
CPC ... A61F 2/442; A61F 2/4425; A61F 2002/443
(Continued)

(56) References Cited

U.S. PATENT DOCUMENTS

| 5,059,193 A | 10/1991 | Kuslich |
|---|---|---|
| 6,039,761 A | 3/2000 | Li et al. |

(Continued)

FOREIGN PATENT DOCUMENTS

| JP | 2004530527 A | 10/2004 |
|---|---|---|
| JP | 2005538754 A | 12/2005 |

(Continued)

OTHER PUBLICATIONS

International Search Report and Written Opinion issued in PCT/US2013/041664 on Aug. 2, 2013.

*Primary Examiner* — Ellen C Hammond
*Assistant Examiner* — Christina Negrellirodrigue
(74) *Attorney, Agent, or Firm* — Fred C. Hernandez; Mintz Levin Cohn Ferris Glovsky and Popeo, P.C.

(57) ABSTRACT

Provided are devices, systems and methods related to articulating interbody cages. The device includes a caudal plate configured to be positioned adjacent a first vertebral endplate within an intervertebral disc space, a cephalad plate configured to be positioned adjacent a second vertebral endplate within the intervertebral disc space; and a first and second sidewall each rotatably coupled to both the caudal and cephalad plates. At least one of the first and second sidewalls includes a hinge element restricted from achieving an on-center or over-center rotational position around the hinge element upon dimensional expansion of the device in at least a first dimension.

26 Claims, 32 Drawing Sheets

Related U.S. Application Data filed on Oct. 24, 2012, provisional application No. 61/794,096, filed on Mar. 15, 2013.

(52) U.S. Cl.
CPC .............. *A61F 2/4455* (2013.01); *A61F 2/46* (2013.01); *A61F 2/4611* (2013.01); *A61F 2002/305* (2013.01); *A61F 2002/3008* (2013.01); *A61F 2002/3037* (2013.01); *A61F 2002/3055* (2013.01); *A61F 2002/30092* (2013.01); *A61F 2002/3093* (2013.01); *A61F 2002/30176* (2013.01); *A61F 2002/30189* (2013.01); *A61F 2002/30266* (2013.01); *A61F 2002/30331* (2013.01); *A61F 2002/30365* (2013.01); *A61F 2002/30372* (2013.01); *A61F 2002/30471* (2013.01); *A61F 2002/30494* (2013.01); *A61F 2002/30504* (2013.01); *A61F 2002/30507* (2013.01); *A61F 2002/30538* (2013.01); *A61F 2002/30556* (2013.01); *A61F 2002/30579* (2013.01); *A61F 2002/30604* (2013.01); *A61F 2002/30626* (2013.01); *A61F 2002/30629* (2013.01); *A61F 2002/30637* (2013.01); *A61F 2002/30736* (2013.01); *A61F 2002/30777* (2013.01); *A61F 2002/30785* (2013.01); *A61F 2002/30904* (2013.01); *A61F 2002/4475* (2013.01); *A61F 2002/4627* (2013.01)

(58) Field of Classification Search
USPC ................ 606/246–249; 623/17.11–17.16
See application file for complete search history.

(56) References Cited

U.S. PATENT DOCUMENTS

| | | | |
|---|---|---|---|
| 6,126,689 A * | 10/2000 | Brett .................. | A61F 2/4455 623/17.15 |
| 6,193,757 B1 | 2/2001 | Foley et al. | |
| 6,395,031 B1 | 5/2002 | Foley et al. | |
| 6,488,710 B2 | 12/2002 | Besselink | |
| 6,833,006 B2 | 12/2004 | Foley et al. | |
| 6,962,606 B2 | 11/2005 | Michelson | |
| 7,070,598 B2 * | 7/2006 | Lim et al. ........... | A61B 17/025 606/99 |
| 7,655,042 B2 | 2/2010 | Foley et al. | |
| 7,722,674 B1 | 5/2010 | Grotz | |
| 7,819,921 B2 | 10/2010 | Grotz | |
| 7,892,286 B2 | 2/2011 | Michelson | |
| 7,985,256 B2 | 7/2011 | Grotz et al. | |
| 7,993,403 B2 | 8/2011 | Foley et al. | |
| 8,070,813 B2 | 12/2011 | Grotz et al. | |
| 8,147,499 B2 | 4/2012 | Zubok et al. | |
| 2003/0171813 A1 | 9/2003 | Kiester | |
| 2003/0208270 A9 | 11/2003 | Michelson | |
| 2005/0131536 A1 | 6/2005 | Eisermann et al. | |
| 2006/0167547 A1 | 7/2006 | Suddaby | |
| 2007/0093901 A1 | 4/2007 | Grotz et al. | |
| 2007/0233254 A1 | 10/2007 | Grotz et al. | |
| 2008/0021559 A1 | 1/2008 | Thramann | |
| 2008/0077242 A1 | 3/2008 | Reo et al. | |
| 2008/0114367 A1 * | 5/2008 | Meyer .................. | A61B 17/025 606/90 |
| 2008/0147194 A1 | 6/2008 | Grotz et al. | |
| 2008/0161933 A1 | 7/2008 | Grotz et al. | |
| 2008/0243255 A1 | 10/2008 | Butler et al. | |
| 2009/0157187 A1 | 6/2009 | Richelsoph | |
| 2009/0216331 A1 | 8/2009 | Grotz et al. | |
| 2009/0222100 A1 | 9/2009 | Cipoletti et al. | |
| 2010/0057204 A1 | 3/2010 | Kadaba et al. | |
| 2010/0145455 A1 | 6/2010 | Simpson et al. | |
| 2010/0145456 A1 | 6/2010 | Simpson et al. | |
| 2010/0185291 A1 | 7/2010 | Jimenez et al. | |
| 2010/0305705 A1 | 12/2010 | Butler et al. | |
| 2011/0035011 A1 | 2/2011 | Cain | |
| 2011/0137420 A1 | 6/2011 | Michelson | |
| 2014/0018922 A1 | 1/2014 | Marino et al. | |

FOREIGN PATENT DOCUMENTS

| | | |
|---|---|---|
| JP | 2007513718 A | 5/2007 |
| JP | 2009509590 A | 3/2009 |
| JP | 2011005264 A | 1/2011 |
| WO | WO-2005/120400 A2 | 12/2005 |
| WO | WO-2009/114523 A1 | 9/2009 |
| WO | WO-2009/125242 A1 | 10/2009 |
| WO | WO-2010/078468 A2 | 7/2010 |

* cited by examiner

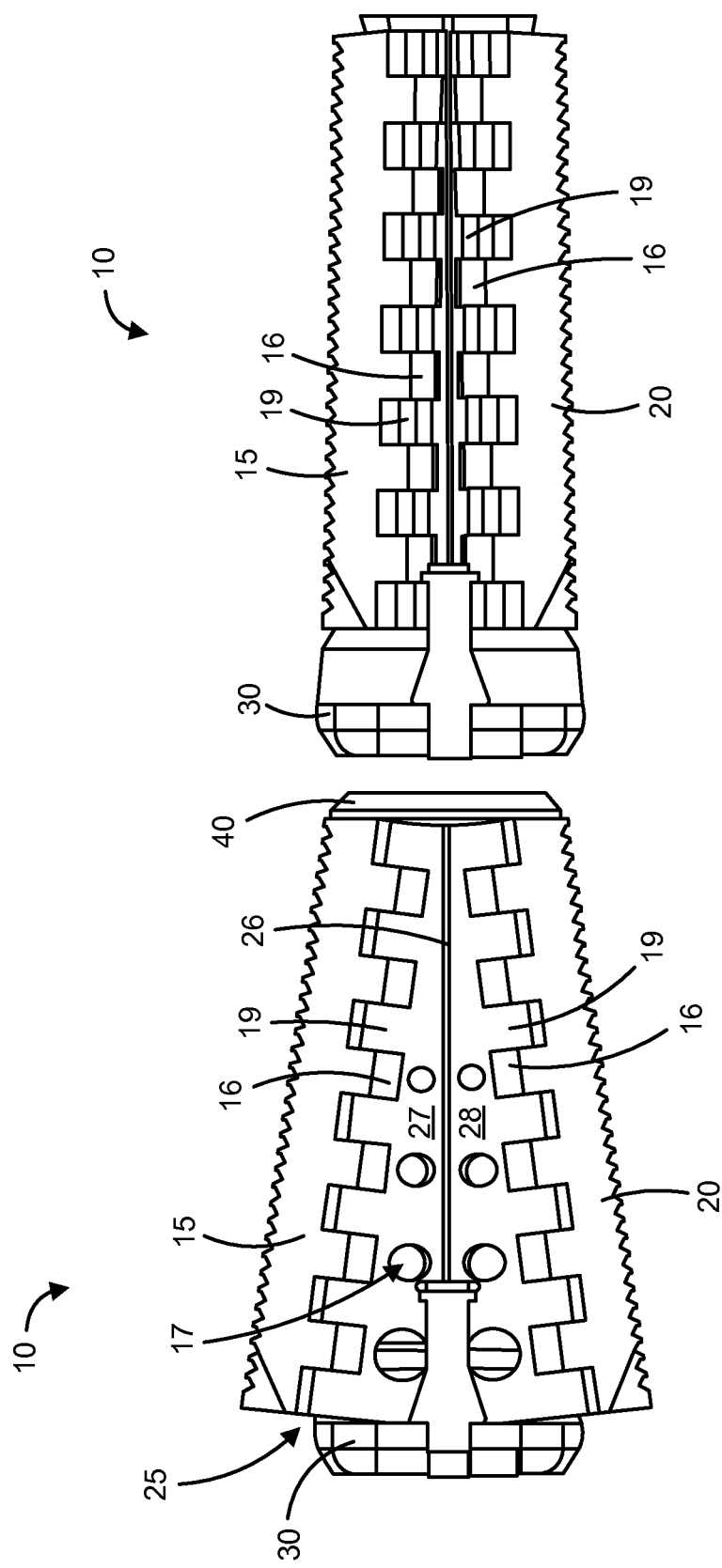

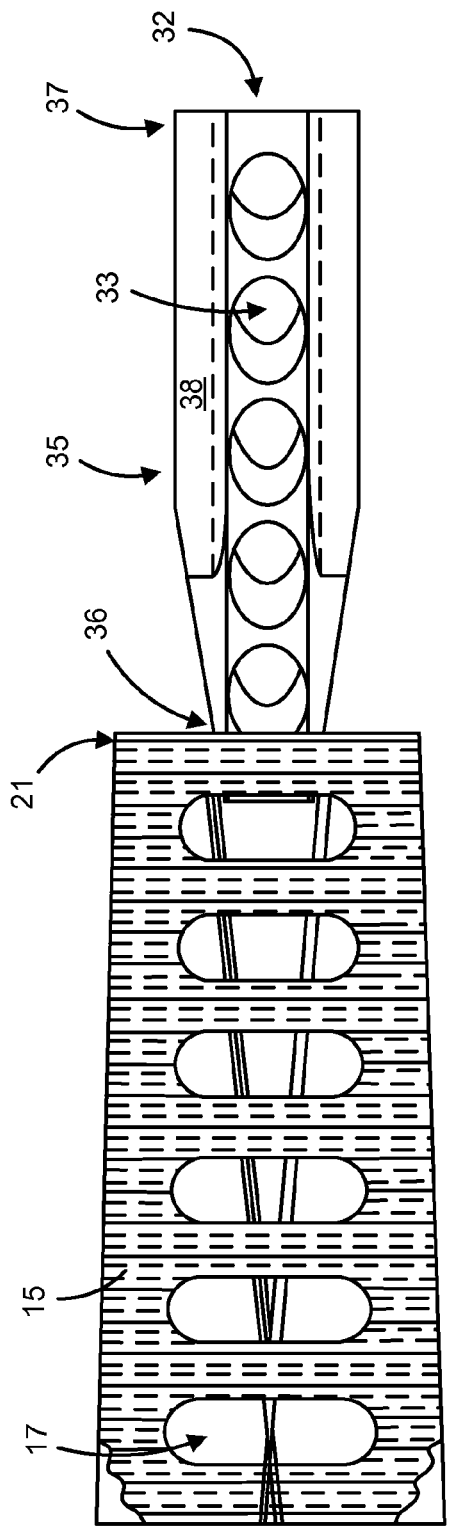
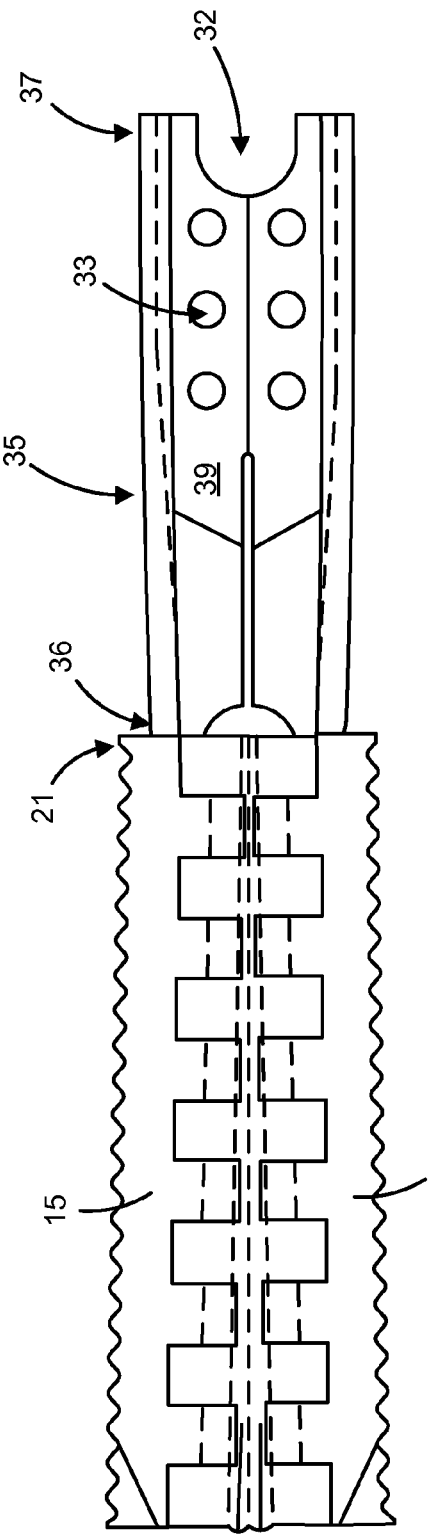
FIG. 3A
FIG. 3B

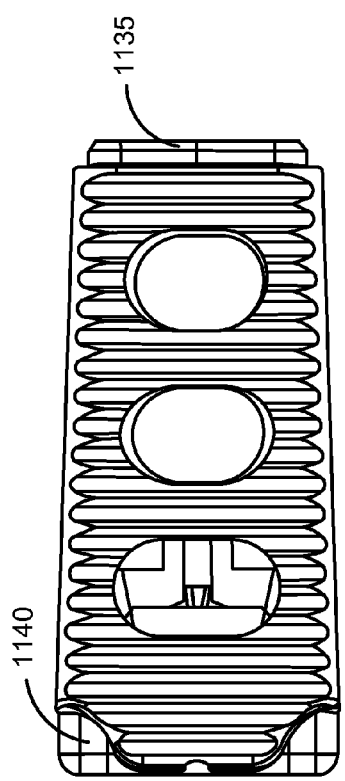
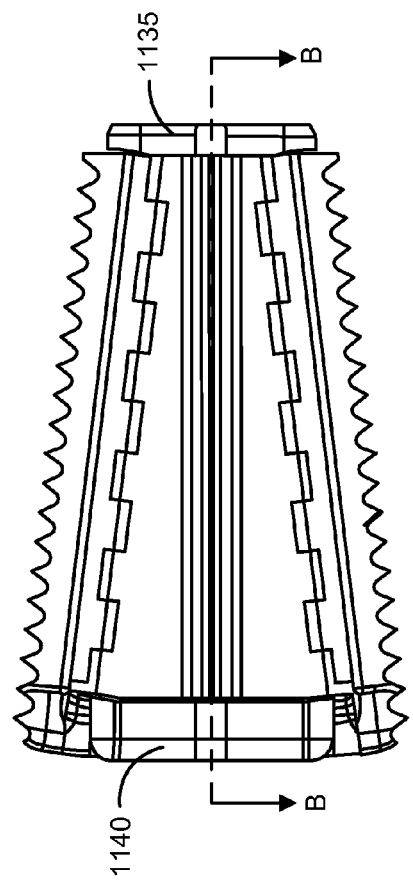
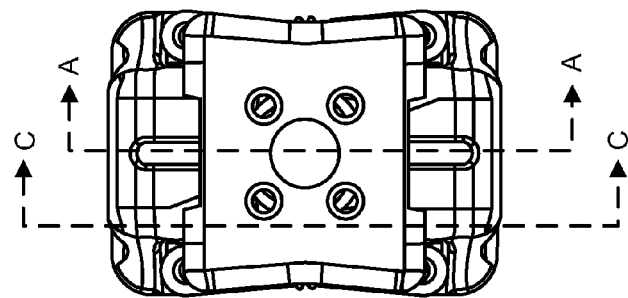
FIG. 11C
FIG. 11D
FIG. 11B

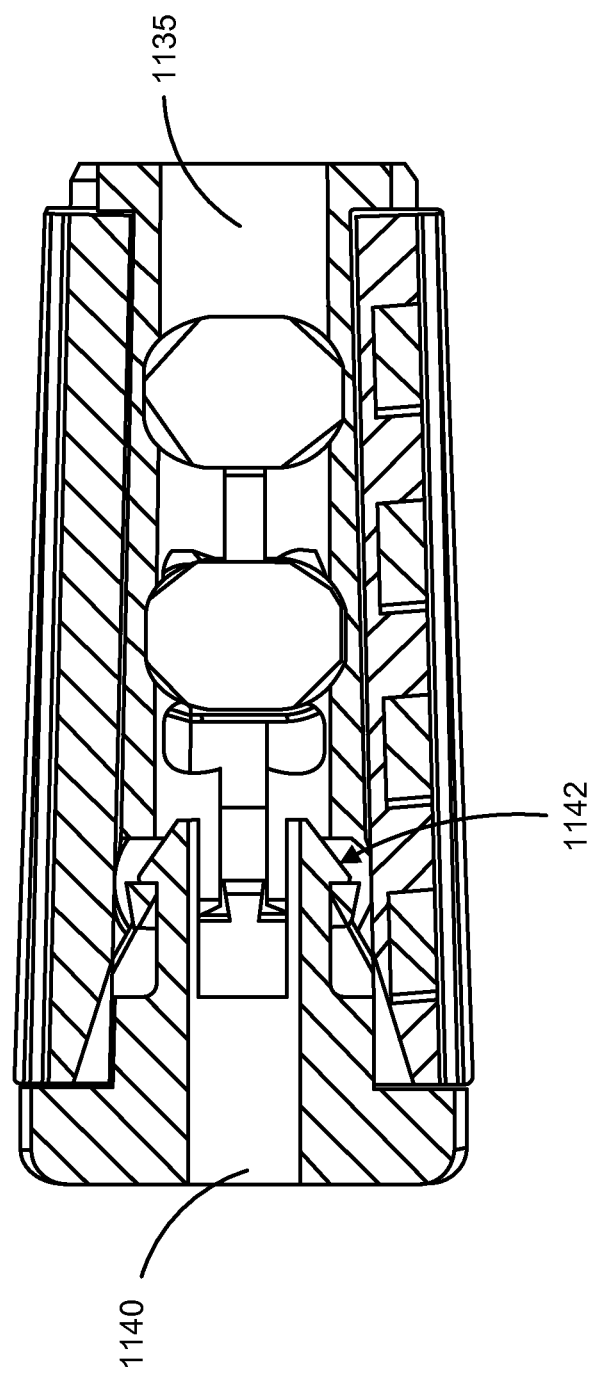

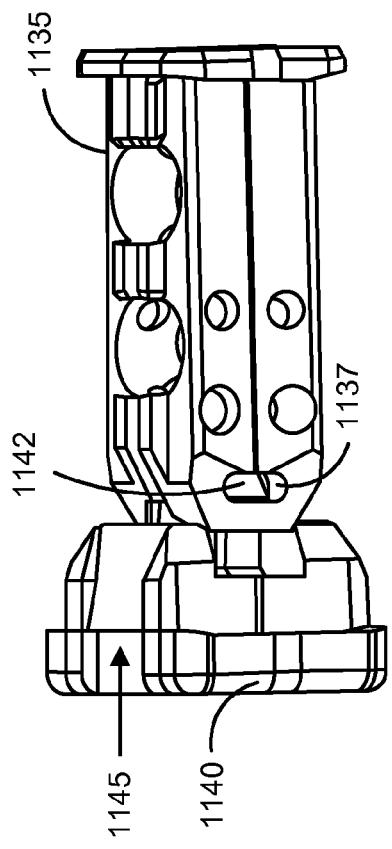
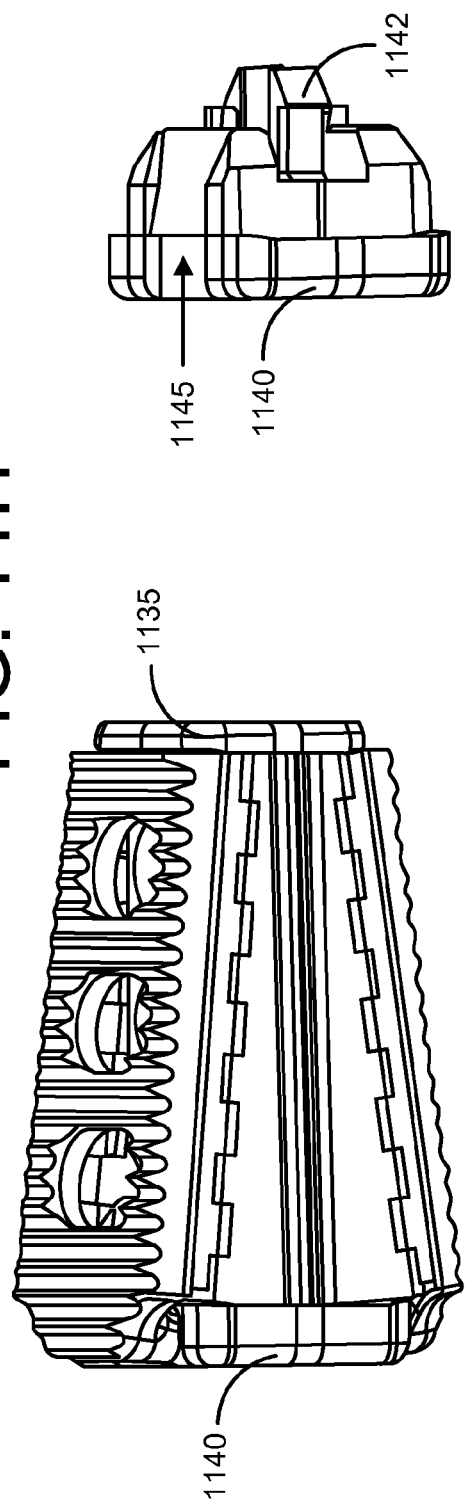
FIG. 11H
FIG. 11I
FIG. 11G

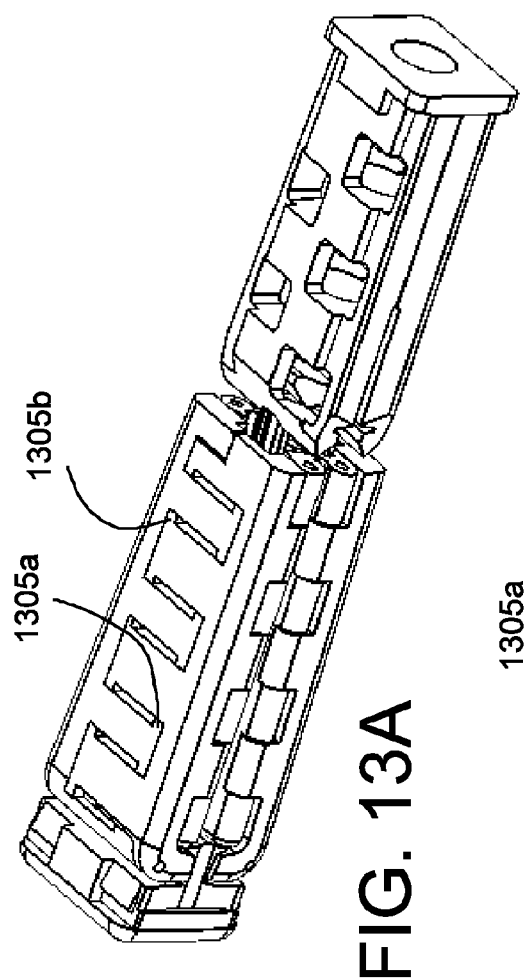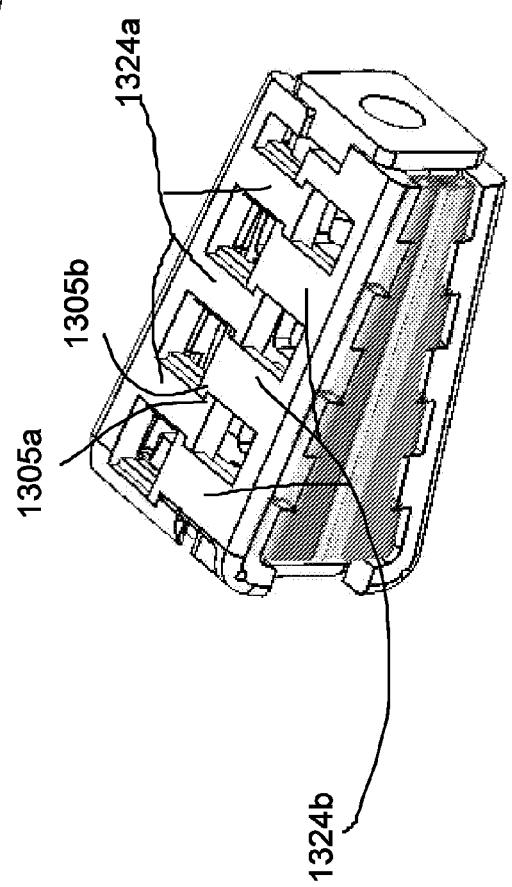
FIG. 13A
FIG. 13B

ARTICULATING INTERBODY CAGE AND METHODS THEREOF

REFERENCE TO PRIORITY DOCUMENTS

This application is a U.S. National Phase application under 37 U.S.C. §371 of Patent Cooperation Treaty Application No. PCT/US2013/041664, filed on May 17, 2013, which claims the benefit of priority under 35 U.S.C. §119(e) of co-pending U.S. Provisional Patent Application Ser. No. 61/649,029, filed May 18, 2012 and U.S. Provisional Patent Application Ser. No. 61/718,143, filed Oct. 24, 2012, and U.S. patent application Ser. No. 61/794,096, filed March 15, 2013. Priority of the aforementioned filing dates is hereby claimed and the disclosures of the provisional patent applications are hereby incorporated by reference in their entirety.

BACKGROUND

A significant number of adults have had an episode of back pain or suffer chronic back pain emanating from a region of the spinal column. A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. Many people suffering from back pain resort to surgical intervention to alleviate their pain.

Disc degeneration can contribute to back pain. With age, the nucleus pulposus of the intervertebral discs tends to become less fluid and more viscous. Dehydration of the intervertebral disc and other degenerative effects can cause severe pain. Annular fissures also may be associated with a herniation or rupture of the annulus causing the nucleus to bulge outward or extrude out through the fissure and impinge upon the spinal column or nerves (i.e. a "ruptured" or "slipped" disc).

In addition to spinal deformities that can occur over several motion segments, spondylolisthesis (i.e. forward displacement of one vertebra over another, usually in the lumbar or cervical spine) is associated with significant axial and/or radicular pain. Patients who suffer from such conditions can experience diminished ability to bear loads, loss of mobility, extreme and debilitating pain, and oftentimes suffer neurological deficit in nerve function.

Failure of conservative therapies to treat spinal pain such as for example bed rest, pain and muscle relaxant medication, physical therapy or steroid injection often urges patients to seek spinal surgical intervention. Many surgical techniques, instruments and spinal disc implants have been described that are intended to provide less invasive, percutaneous, or minimally-invasive access to a degenerated intervertebral spinal disc. Instruments are introduced through the annulus for performing a discectomy and implanting bone growth materials or biomaterials or spinal disc implants within the annulus. One or more annular incisions are made into the disc to receive spinal disc implants or bone growth material to promote fusion, or to receive a pre-formed, artificial, functional disc replacement implant.

Extensive perineural dissection and bone preparation can be necessary for some of these techniques. In addition, the disruption of annular or periannular structures can result in loss of stability or nerve injury. As a result, the spinal column can be further weakened and/or result in surgery-induced pain syndromes.

There are a variety of surgical approaches to the lumbar spine, including the Posterior Lumbar Interbody Fusion approach (i.e. PLIF procedure), the Transforaminal Lumbar Interbody Fusion approach (i.e. TLIF procedure), the Lateral Lumbar Interbody Fusion approach (i.e. LLIF procedure), and the Anterior Lumbar Interbody Fusion approach (i.e. ALIF procedure). Each of these various surgical approaches involves surgical dissection paths that necessitate nerve and or vascular retraction. The desire to restore disc space height and create lordosis through anterior distraction is in conflict with the application of a fixed height interbody spacer through the limitations of various minimally invasive surgical approaches and in particular those utilizing posterior approaches such as the PLIF and TLIF approach (and to a lesser extent, the LLIF and ALIF approaches). In addition, the larger the "foot-print" of the interbody spacer, the less likely it will subside. This is not only due to reduced endplate pressure but also better load bearing bone near the perimeter of the endplate (versus the central region).

SUMMARY

In one aspect, provided are devices that include a caudal plate configured to be positioned adjacent a first vertebral endplate within an intervertebral disc space, a cephalad plate configured to be positioned adjacent a second vertebral endplate within the intervertebral disc space; and a first and second sidewall each rotatably coupled to both the caudal and cephalad plates. At least one of the first and second sidewalls includes a hinge element restricted from achieving an on-center or over-center rotational position around the hinge element upon dimensional expansion of the device in at least a first dimension.

The devices described herein can further include at least one brace element configured to be positioned within the confines of the caudal and cephalad plates and the first and second sidewalls of the device. The at least one brace element can resist compressive loading of the device along an axis or axes extending between the caudal and cephalad plates via the restriction of at least one of the first and second sidewall's under-center rotated hinge element from displacing toward the interior of the device. At least one of the caudal plate, the cephalad plate, first sidewall and the second sidewall can be radiolucent. Osteoinductive, osteoproliferative, and/or osteoconductive material can extend from the first vertebral endplate to the second vertebral endplate. At least one of the caudal plate and the cephalad plate can have a textured external surface. The first dimension can be along an axis or arc other than a caudal-cephalad dimension. The at least one brace element can include at least one contiguous osteoconductive channel extending from a caudal surface of the brace element to a cephalad surface of the brace element. The device can further include a buttress element having an upper surface coupled to the caudal plate and a lower surface coupled to the cephalad plate. One or more apertures can extend through the buttress element. The device can further include one or more pliable tethers extending through the one or more apertures in the buttress element. The one or more pliable tethers can be configured to apply a pulling force on the device in a direction away from the anterior buttress as a pushing force is applied on the at least one brace element in a direction towards the anterior buttress to maintain a net zero force on the device during insertion of the at least one brace element within the confines of the caudal and cephalad plates. The net zero force can prevent migration of the device between the first and second vertebral endplates during expansion of the device with the at least one brace element. The device can enlarge in a second dimension. The first dimension can include a caudal-to-cephalad dimension and the second dimension can include medial-lateral dimension or an anterior-to-posterior dimension. The caudal and cephalad plates each can include a first portion slideably coupled to a second portion. The first portions and second portions can each include one or more fingers slideably interdigitated with one another. Each of the one or more fingers can further include a stop element configured to abut one another upon sliding translation to prevent overexpansion along the second dimension.

In an interrelated aspect, provided herein are devices including a caudal plate positioned adjacent a first vertebral endplate within an intervertebral disc space; a cephalad plate positioned adjacent a second vertebral endplate within the intervertebral disc space; a first and second sidewall each rotatably coupled to both the caudal and cephalad plates; and at least one brace element generally positioned within the confines of the caudal and cephalad plates as well as the first and second sidewalls of the device. The brace element resists compressive loading of the device along an axis or axes extending between caudal and cephalad plates. The device is configured to be inserted into the intervertebral disc space in a first dimension and subsequently expanded to a second dimension larger than the first dimension.

At least one of the first and second sidewalls can include a hinge element. The hinge element can be restricted from achieving an on-center or over-center rotational position around the hinge element upon dimensional expansion of the device in at least a first dimension. The brace element can restrict at least one sidewall's under-center rotated hinge element from displacing toward the interior of the device. At least one of the caudal plate, cephalad plate, first sidewall and second sidewall can be relatively radiolucent. Osteoinductive, osteoproliferative, and/or osteoconductive material can extend from endplate to endplate. External surfaces of the caudal and cephalad plates can be textured. Dimensional expansion of the device can include expansion along an axis or arc other than caudal-cephalad expansion.

In an interrelated aspect, provided herein are devices including a caudal plate positioned adjacent a first vertebral endplate within an intervertebral disc space; a cephalad plate positioned adjacent a second vertebral endplate within the intervertebral disc space; at least one lateral wall rotatably coupled to the caudal and cephalad plates; and an internal brace element. The device is configured to be inserted into the intervertebral disc space in a first dimension and subsequently expanded to a second dimension larger than the first dimension and expanded along a cephalad-caudal axis or arc through a wedging effect of introducing the internal brace element.

Introducing the internal brace element can include a push-pull or net zero displacement mechanism along an axis of introduction of the brace. The lateral wall can include a hinge element. The hinge element can be restricted from achieving an on-center or over-center rotational position around the hinge element upon dimensional expansion of the device in at least a first dimension. At least one of the caudal plate, cephalad plate, and the at least one lateral wall can be relatively radiolucent. Osteoinductive, osteoproliferative, and/or osteoconductive material can extend from endplate to endplate. External surfaces of the caudal and cephalad plates can be textured. Dimensional expansion of the device can include expansion along an axis or arc other than caudal-cephalad expansion.

In an interrelated aspect, provided herein are methods for expanding a device for displacing adjacent bone elements.

The method includes inserting a wedging element within a frame of the device positioned between adjacent bone elements using an insertion tool. The method also includes advancing the wedging element using the insertion tool along an axis while concurrently restraining the frame from advancing along the axis using the insertion tool. The method also includes expanding the frame of the device with the wedging element to impose a displacing force by the frame on the adjacent bone elements.

The adjacent bone elements being displaced can be the vertebrae adjoining an intervertebral disc space. Advancing the wedging element can include threadlessly engaging the wedging element and the frame. The axis can be co-linear with a long axis of the insertion tool used to advance the wedging element while restraining the frame. Restraining the frame can include employing one or more tethers attached to the frame and the insertion tool. Advancing the wedging element using the insertion tool can include employing a piston or plunger of the insertion tool to displace the wedging element along an axis of the insertion tool. The frame can includes a hinge element that articulates during advancing the wedging element.

In an interrelated aspect, provided herein are systems for expanding a device for displacing adjacent bone elements. The system includes an insertion tool; an expandable frame surrounding an internal volume and positionable between adjacent bone elements; and a wedging element positionable within the frame. The insertion tool is configured to expand the frame into a larger dimension to impose a displacing force on the adjacent bone elements by advancing the wedging element into the internal volume of the expandable frame along an axis while concurrently restraining the expandable frame from advancing along the axis.

The adjacent bone elements being displaced can be the vertebrae adjoining an intervertebral disc space. An outer surface of the wedging element and an inner surface of the expandable frame contacting the outer surface of the wedging element can be both threadless. The axis can be co-linear with a long axis of the insertion tool. The system can include one or more tethers attached to at least the expandable frame employable to restrain the frame. The insertion tool can further include a piston or plunger configured to advance the wedging element along an axis of the insertion tool. The expandable frame can include a hinge element that articulates during advancing the wedging element.

In an interrelated aspect, provided herein is a device including a caudal plate positioned adjacent a first vertebral endplate within an intervertebral disc space; a cephalad plate positioned adjacent a second vertebral endplate within the intervertebral disc space; and a first and second sidewall each rotatably coupled to both the caudal and cephalad plates. At least one of the first and second sidewalls includes a hinge element restricted from achieving an on-center or over-center rotational position around the hinge element upon dimensional expansion of the device in at least a first dimension. At least one of the first and second sidewalls includes a meeting edge surface having a first interlocking element configured to abut with a corresponding second interlocking element positioned on an opposing meeting edge surface.

The first and second interlocking elements can resist translational movement of the first and second sidewalls due to application of a compressive load or shear loading of the first and second sidewalls when the device is fully dimensionally expanded and under compression between the first and second vertebral endplates. The device can further include at least one brace element generally positioned within the confines of the caudal and cephalad plates as well as the first and second sidewalls of the device. The brace element can resist compressive loading of the device along an axis or axes extending between the caudal and cephalad plates via the restriction of at least one of the first and second sidewall's under-center rotated hinge element from displacing toward the interior of the device. The device can further include an anterior buttress comprising a surface having a snap lock feature that engages one or both of the caudal and cephalad plates. The brace element can further include a surface having a snap lock feature that engages the snap lock feature of the anterior buttress.

BRIEF DESCRIPTION OF THE DRAWINGS

Reference is made to the following description, taken in conjunction with the accompanying drawings, in which like reference characters refer to like parts throughout.

FIG. 2A is a side view of the device in FIG. 1A;

FIG. 2B is a side, partial view of the device in FIG. 1B;

FIG. 3A is a top view of an implementation of the device;

FIG. 3B is a side view of the device in FIG. 3A;

FIG. 11B is an end view of the device of FIG. 10.

FIG. 11C is a top view of the device of FIG. 10.

FIG. 11D is a side view of the device of FIG. 10.

FIG. 11E is a cross-sectional view of the device of FIG. 10 taken along line B-B of FIG. 11D.

FIG. 11G is a side, perspective view of the device of FIG. 10.

FIG. 11H is a side, perspective view of the buttress and internal brace of the device of FIG. 10 coupled together.

FIG. 11I is a side, perspective view of the buttress of the device of FIG. 10.

FIGS. 13A and 13B show another implementation of an articulating device having expansion stop elements.

It is to be understood that implants described herein may include features not necessarily depicted in each figure. In some embodiments, an endplate engaging surface of any implant may have regularly or irregularly spaced protrusions of uniform or various shapes and sizes to facilitate retention of the implant in a desired position between vertebrae.

DETAILED DESCRIPTION

Disclosed are articulating interbody devices and systems that are adapted to stabilize and fuse bony structures. The devices and systems described herein are designed for minimally-invasive interbody fusion procedures and can be releasably deployed through a variety of minimally-invasive access channels or small access ports into the intervertebral disc space, for example. The devices and systems described herein can be used for a variety of surgical applications and implanted by a variety of surgical approaches using minimally-invasive access channels (PLIF, TLIF, LLIF, and ALIF, etc.) The devices can also be inserted anteriorly as well as posteriorly and/or laterally.

As used herein the term anterior or anteriorly generally means from the front side or in the direction of the abdomen and posterior or posteriorly generally means from the backside or in the direction of the backside. Cephalad, superior, and upper generally mean towards a patient's head and caudal, inferior, and lower generally mean away from a patient's head. Proximal as used herein generally means nearer to a surgeon's point of reference and distal generally means further away from the surgeon's point of reference.

The interbody devices and systems described herein can be expanded from a reduced dimension prior to delivery for a minimally-invasive introduction into an enlarged dimension upon insertion between bony structures. The devices and systems described herein can have an enlarged dimension along at least one, two or more planes or dimensions. Although the devices and systems described herein can undergo expansion, the expansion can be limited such that rotation is generally less than on-center. Further, the devices and systems described herein can include an internal buttress element for very high load bearing capacity that can be implanted using a push-pull mechanism resulting in a net zero force and displacement of the device between the bony structures.

Figures 1A, 1B:
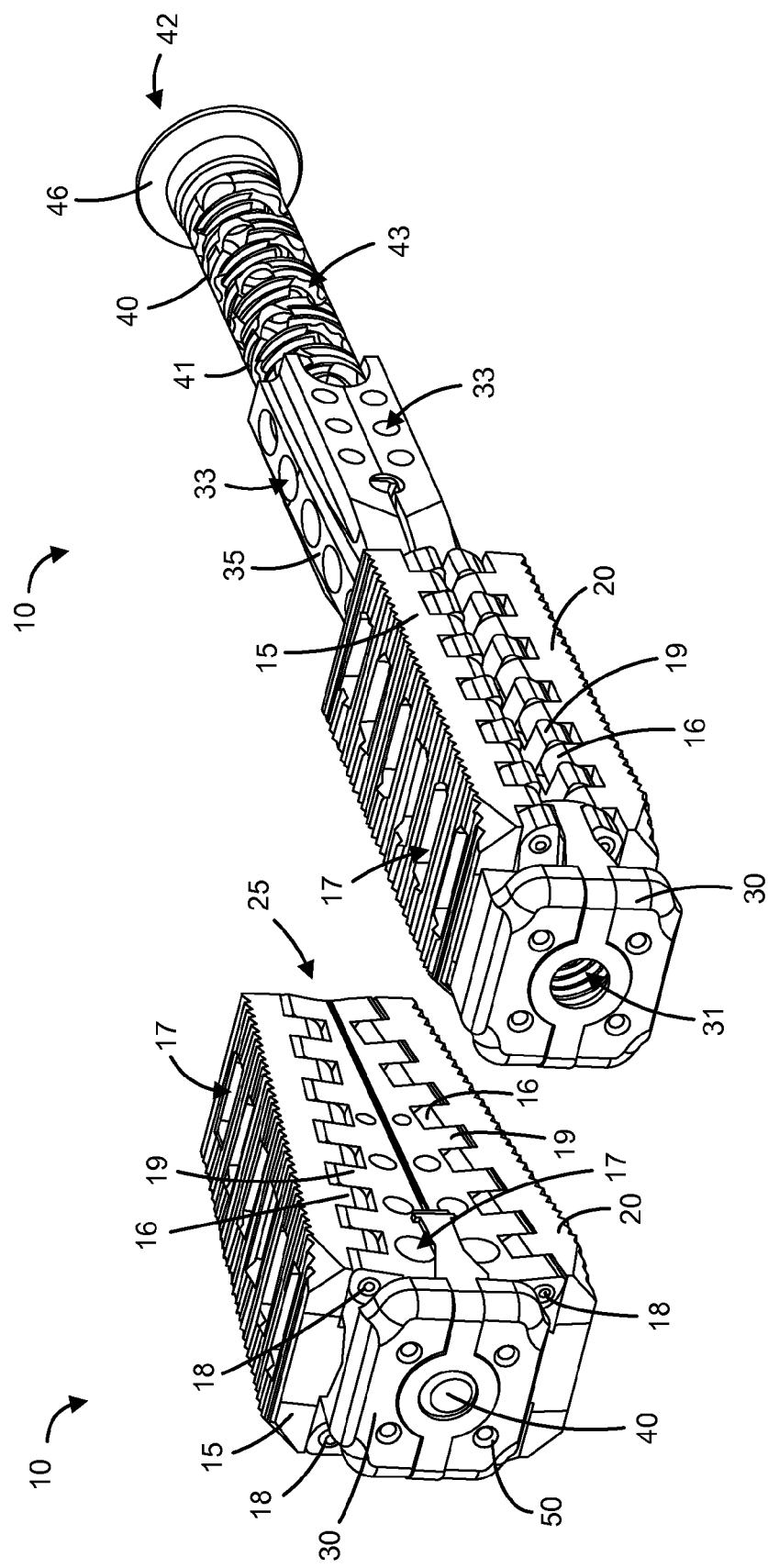
FIG. 1A illustrates an implementation of an articulating interbody device in a deployed, expanded dimension configuration.
FIG. 1B illustrates the articulating interbody device of FIG. 1A in an insertion, reduced dimension configuration.

Now with respect to the figures, specific implementations of the articulating interbody devices will be described. FIGS. 1A and 1B illustrate an implementation of an articulating interbody device 10. The device 10 can have a frame including an upper plate 15 and a lower plate 20 connected by two articulating sidewalls 25 and surrounding an internal volume. The device 10 can include an anterior buttress 30, a wedging element or internal brace 35 and a locking element 40 as will each be described in more detail below.

When deployed between adjacent vertebrae, the upper plate 15 can be in contact with an endplate of the superior or more cephalad vertebra and the lower plate 20 can be in contact with an endplate of the inferior or more caudal vertebra. The upper and lower plates 15, 20 can each have an external surface that is textured for better association of the device 10 with the endplates. The upper and lower plates 15, 20 can also include one or more apertures 17 extending through to the internal volume of the device 10.

As best shown in FIGS. 2A and 2B, the upper and lower plates 15, 20 can be rotationally coupled to the sidewalls 25. The upper plate 15 can include a plurality of axially-aligned hinge knuckles 16 on each of its lateral sides that extend downward. Similarly, the lower plate 20 can include a plurality of axially-aligned hinge knuckles 16 on each of its lateral sides that extend upward. The hinge knuckles 16 of the upper plate 15 can interdigitate with corresponding upwardly-extending hinge knuckles 19 of the sidewalls 25 forming a pair of axially-extending bores. The hinge knuckles 16 of the lower plate 20 can interdigitate with corresponding downwardly-extending hinge knuckles 19 on the sidewalls 25 forming a second pair of axially-extending bores. The axially-extending bores can receive an axis pin or pintle 18 forming a pivot point around which the knuckles 16, 19 can rotate during expansion of the device 10 (see FIGS. 1A-1B).

As best shown in FIG. 2A, each of the sidewalls 25 can include an upper sidewall portion 27 and a lower sidewall portion 28 connected by a hinge element 26 extending along the length of the sidewalls 25. The hinge element 26 can allow for the device 10 to have a reduced dimension appropriate for minimally-invasive insertion and an enlarged dimension such as upon distraction and deployment in the target disc space location. The device 10 can increase in a first dimension such as the caudal-cephalad dimension upon articulation of the hinge element 26. The hinge element 26 can include an eccentrically positioned "living hinge" or a thin flexure bearing made from the same material as the upper and lower portions 27, 28 of the sidewalls 25. The hinge element 26 can allow for the upper and lower sidewall portions 27, 28 to bend or pivot along the line of the hinge element 26 relative to each other with minimal friction, wear or fatigue.

The hinge element 26 can be designed such that the upper and lower sidewall portions 27, 28 are prevented from articulating past a certain rotational position. For example, the hinge element 26 can fold inward in a first low-profile configuration and upon expansion to a higher profile configuration can be prevented from articulating to an on-center or over-center rotational position such that even at maximum device expansion, the sidewall portions 27, 28 are aligned slightly under-center relative to each other and angled towards the internal volume (see FIG. 1A). The upper and lower sidewall portions 27, 28 can include corresponding meeting edge surfaces that abut and/or mechanically interlock thereby preventing further pivoting beyond the under-center rotational position. As such, when the device is under compression such as from the superior and inferior vertebrae, the device 10 is biased to collapse inwardly as opposed to outwardly upon compression loading.

Still with respect to FIGS. 2A-2B, the sidewalls 25 can have a shape such that upon deployment and expansion of the device 10 in the disc space a proper lordosis is provided to the region of the spine. For example, the posterior extents of the sidewalls 25 can be tapered relative to the anterior extents of the sidewalls 25 such that the device 10 provides greater distraction of the adjacent endplates anteriorly than posteriorly resulting in convexity of the spine segment anteriorly and concavity posteriorly (as viewed in the sagittal plane) or lordosis. It should be appreciated that one sidewall 25 can have a dimension (e.g. height or length) that differs from the dimension of the second sidewall 25. The dissimilar dimensions between the sidewalls can provide an advantage, for example, when positioning an oblique interbody device (obliquely positioned relative to the sagittal plane of the disc space) as is frequently done with TLIF approaches. The disparity in dimensions accommodates the oblique orientation in effecting a lordotic inclination that is oriented in the true sagittal plane. Further, a disparity in sidewall length can increase the potential surface support or footprint of the device.

As mentioned above, the device 10 can be biased to collapse inwardly upon compressive load on the upper and lower plates 15, 20 due to the under-center rotation of the sidewall portions 27, 28 relative to one another. As shown in FIG. 1B, an internal brace 35 can be positioned within the internal volume of the device 10 to internally support loading between the upper and lower plates 15, 20 and the sidewalls 25. FIG. 3A is a top view and FIG. 3B is a side view of the device and the internal brace 35 prior to insertion in the internal volume. As best shown in FIG. 3A, the leading end 36 of the brace 35 can have a more narrow dimension compared to the trailing end 37 of the brace 35 providing the internal brace 35 with a wedge shape. The leading end 36 of the brace 35 can be positioned within the internal volume of the device at the posterior end 21 of the reduced dimension device 10 (i.e. prior to expansion). The wedge shape of the internal brace 35 can be configured to urge the upper and lower sidewall portions 27, 28 to pivot around hinge element 26 into the expanded configuration as the internal brace 35 is urged distally and inserted into the internal volume of the device 10. The internal brace 35 can be advanced into the frame of the device in a threadless manner such that the brace 35 and the frame of the device engage without a thread form. The side surfaces 39 of the internal brace 35 can abut against the hinged sidewalls 25 including surfaces adjacent to the hinge element 26 axes. The side surfaces 39 can also apply expansive pressure upon the upper and lower plates 15, 20 as well as the hinged sidewalls 25 upon wedging to deploy the expansion of the device.

The internal brace 35 can be deployed using a push-pull mechanism of distraction force as will be described in more detail below. The device 10 can include one or more pliable tethers 55 such as sutures, cables, wires or other element coupled to the device and/or the insertion tool. The tethers 55 can extend through a plurality of apertures 50 in the anterior buttress 30. The tethers 55 can be used to apply a pulling force on the anterior buttress 30 in the proximal direction (e.g. toward the surgeon deploying the device) while the internal brace 35 is advanced distally (e.g. away from the surgeon deploying the device) into the interior of the initially collapsed device 10. The tethers 55 can be used to apply a pulling force in the distal direction away from the anterior buttress 30 while the internal brace 35 is advanced into the interior of the initially collapsed device 10 using, for example, an elongate element extending through the delivery cannula. This allows for the device 10 to be deployed by applying push and pull forces simultaneously resulting in a net zero force and displacement of the device within the disc space. The device 10 is prevented from migration during introduction of the internal brace 35 by pulling on the tethers 55 coupled to the anterior buttress 30. The internal brace 35 along with the anterior buttress 30 provides internal support loading between the upper and lower plates 15, 20. The anterior buttress 30 can also provide an internal and external buttressing of the sidewalls 25 in the expanded position.

Figure 4:
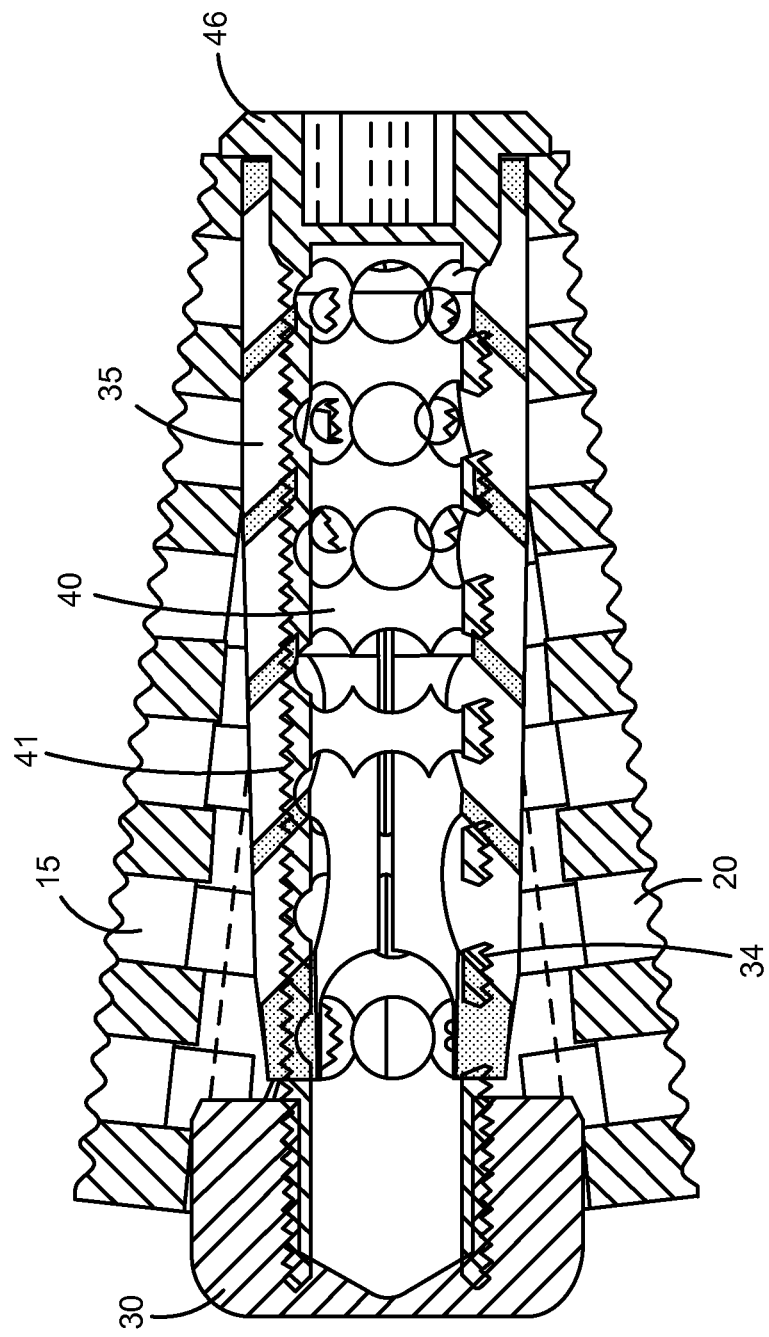
FIG. 4 is a cross-sectional view of the device in FIG. 1A.

As best shown in FIG. 4, once the internal brace 35 is positioned within the internal volume of the device 10, a locking element 40 can be inserted through a central bore 32 of the internal brace 35 to engage and securely associate the components of the assembled and expanded device 10 preventing inadvertent withdrawal of the internal brace 35 from the internal volume of the device 10. The locking element 40 can be an elongate element having thread forms 41 on its outer surface and a proximal end 46 configured to interface with a delivery tool. The thread forms 41 of the locking element 40 can engage with one or more portions of the central bore 32 of the internal brace 35 having complementary threads 34. The anterior buttress 30 can also include a central threaded bore 31 such that receives the thread form 41 near a distal end of the locking element 40 upon tightening of the locking element 40.

The internal brace 35 and the locking element 40 can each include a central bore 32, 42 and a plurality of through-holes 33, 43 extending from the central bores 32, 42 through one or more respective surfaces of the internal brace 35 or locking element 40. The bores 32, 42 and through-holes 33, 43 can allow for the containment and positioning of filler material such as osteoinductive, osteoproliferative and/or osteoconductive material. The filler material can be delivered along the axis of introduction through a delivery cannula into the internal volume of the expanded device 10. The filler material can fill voids within the device 10. The through-holes 33, 43 of the internal brace 35 and the locking element 40 can align with through-holes 17 in the upper and lower plates 15, 20 as well as through-holes 17 in the sidewalls 25 such that the material can extend from endplate to endplate and laterally within the disc space providing for bone growth from the areas immediately adjacent to the external perimeter of the device into and through the device.

Figure 5A:
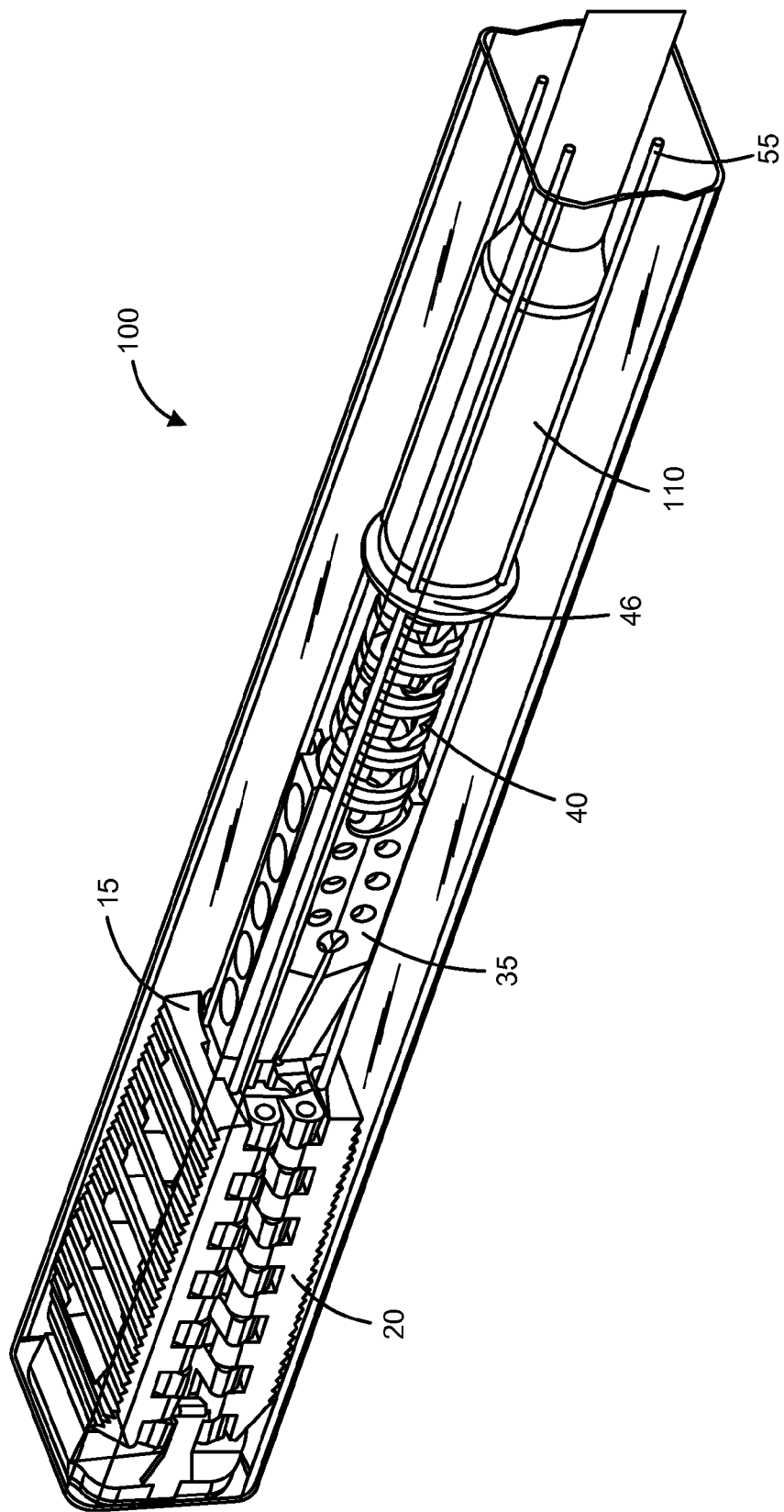
FIGS. 5A-5E are perspective views of the deployment of the device in FIG. 1A.
Figure 5B:
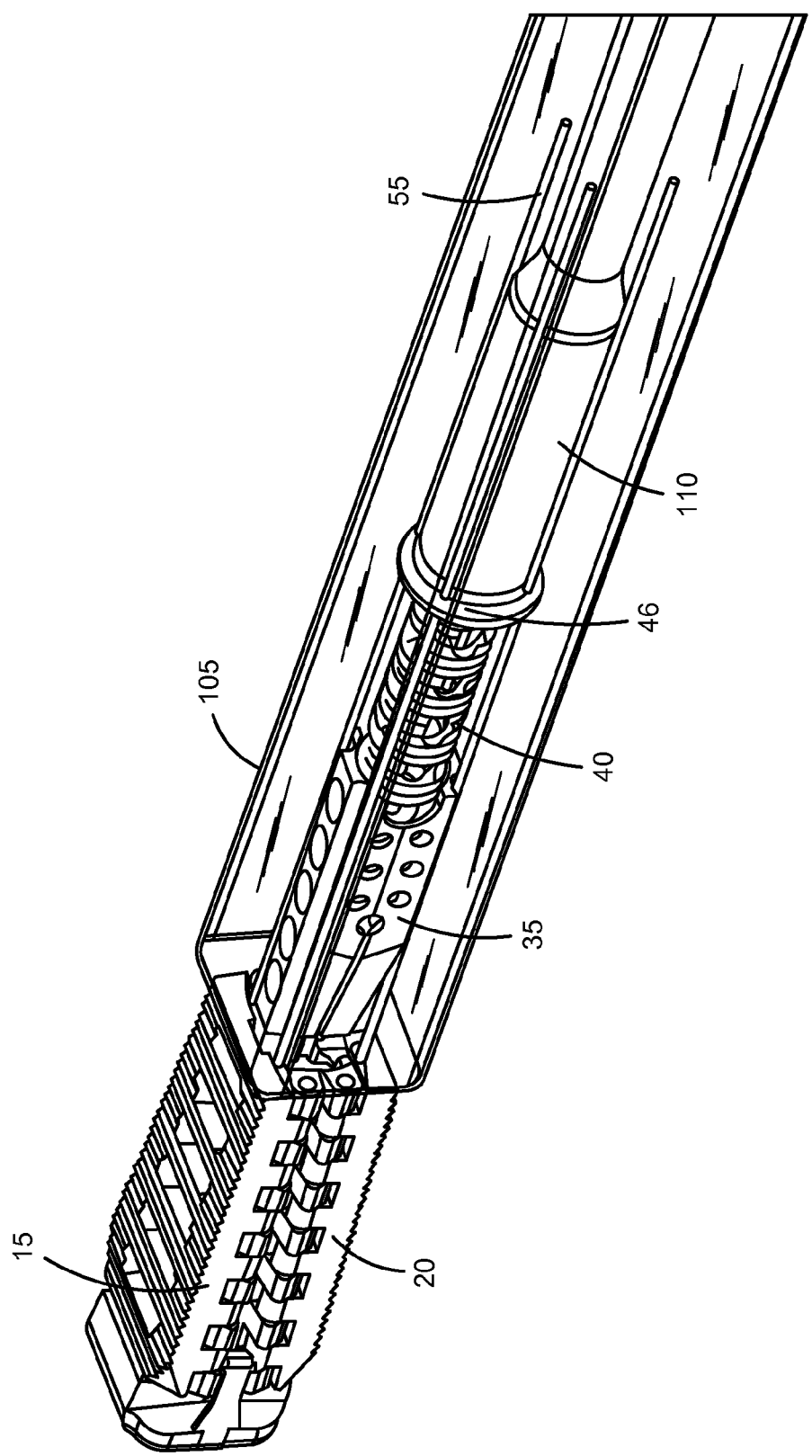
Figure 5C:
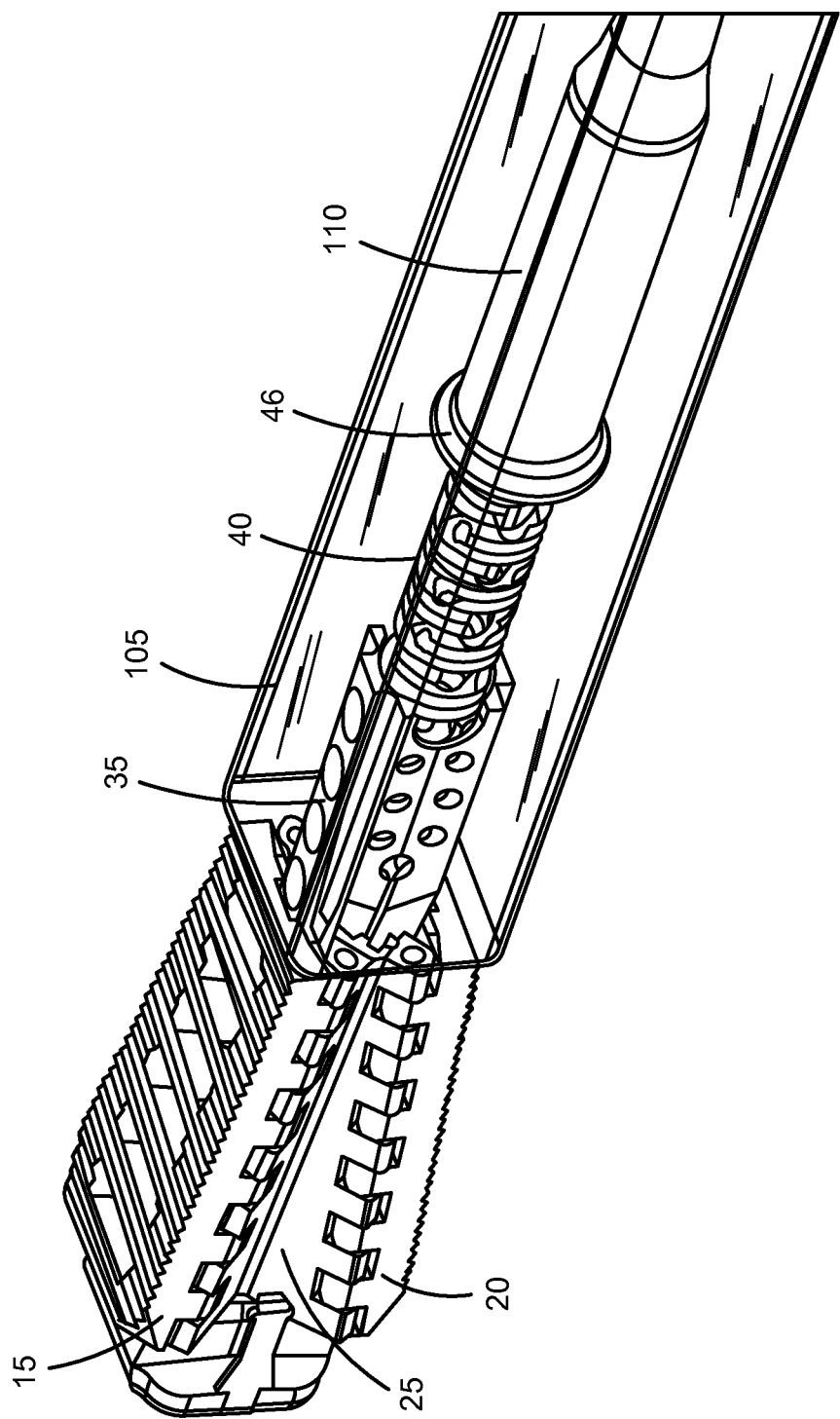
Figure 5D:
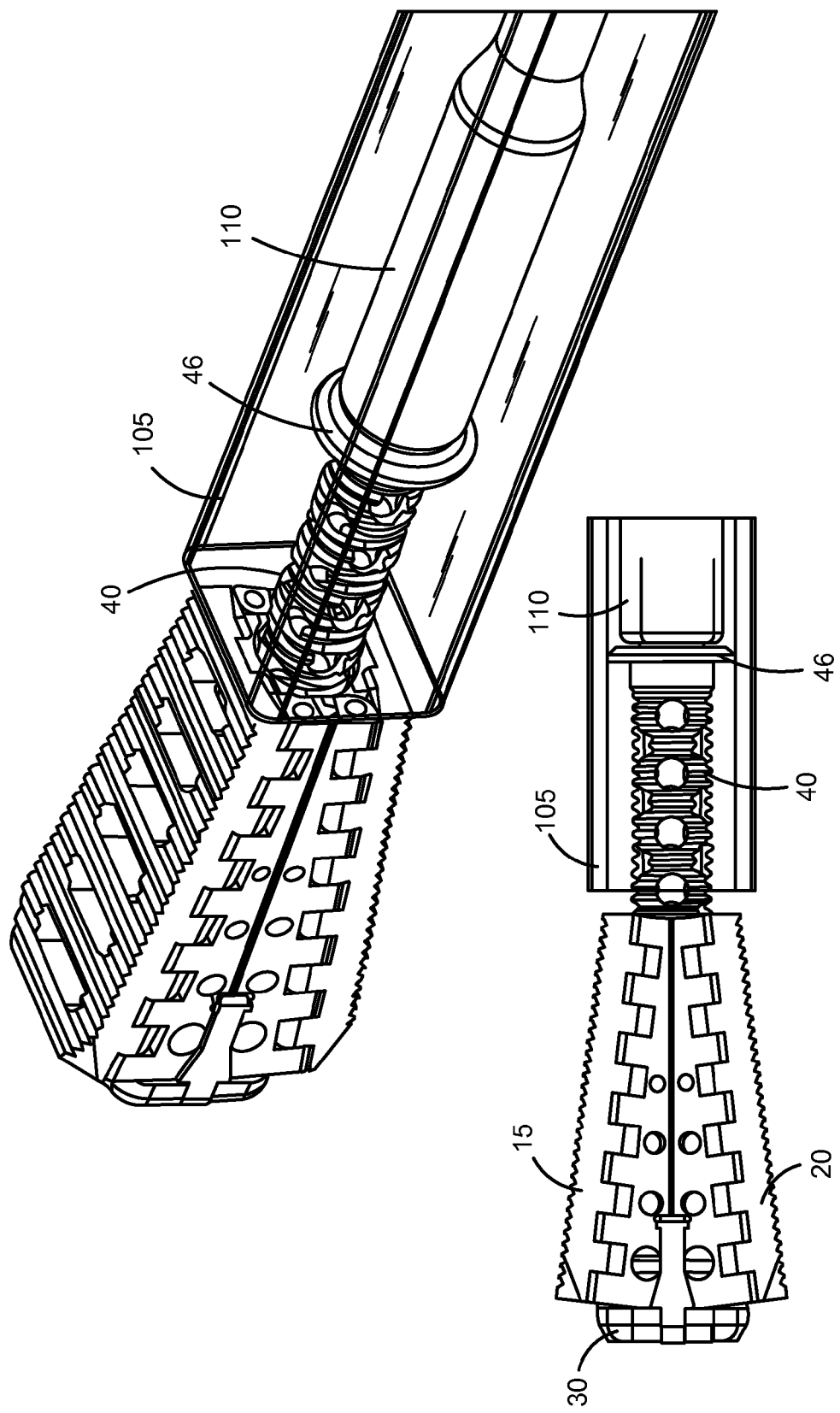
Figure 5E:
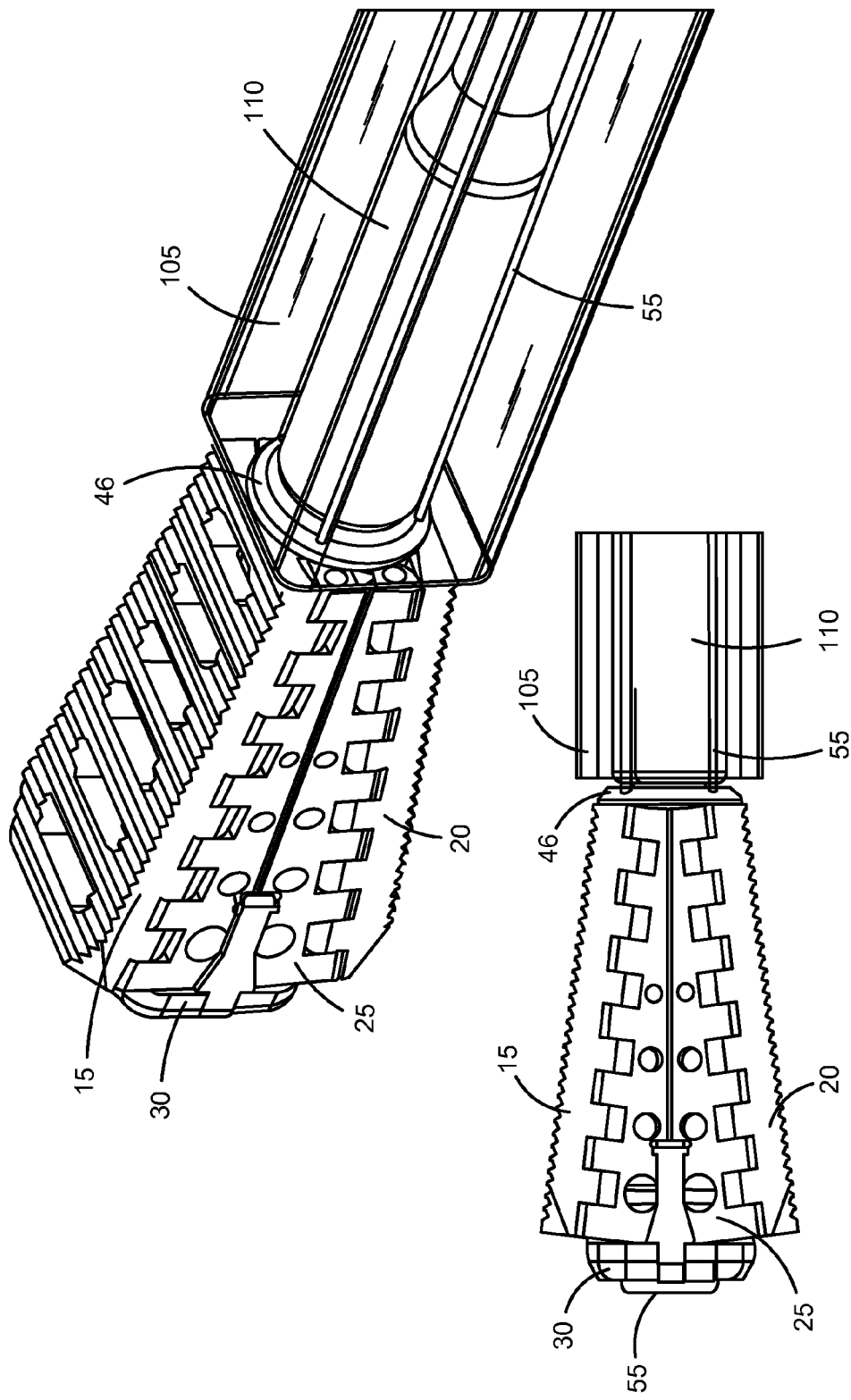

FIGS. 5A-5E illustrate a deployment system 100 for delivery and expansion of the articulating interbody device 10. The deployment system 100 can include a delivery cannula 105 and an elongate element 110 extending through the internal channel of the delivery cannula 105. The elongate element 110 can be used as a piston or plunger of the insertion tool to advance the internal brace 35 into the internal volume of the device. The internal channel of the delivery cannula 105 can accommodate the dimensions of the reduced dimension device 10. The elongate element 110 can have a distal end configured to engage the proximal end 46 of the locking element 40. As shown in FIG. 5A, the locking element 40 can be at least partially threaded into the central bore 32 of the internal brace 35 and the leading end 36 of the internal brace 35 can be positioned within a portion of the internal volume near the posterior end 21 of the reduced dimension device 10. The elongate element 110 can be extended in a distal direction such that the device 10 extends beyond the distal end of the delivery cannula 105 (FIG. 5B). The tethers 55 coupled through the apertures 50 in the anterior buttress 30 can extend proximally through the internal channel of the delivery cannula 105. A proximal pulling force can be applied to the tethers 55 as the internal brace 35 is urged in a distal direction using the elongate element 110 to partially expand the device 10 (FIG. 5C). The device 10 can achieve its full under-center expanded configuration upon complete insertion of the internal brace 35 (FIG. 5D). The elongate element 110 can be used to thread the locking element 40 within the central bore 32 of the internal brace and the central bore 31 of the anterior buttress 30 achieving a final locking of the device 10 (FIG. 5E). Once the device is expanded, optionally filled, and locked, it can be releasably deployed. The elongate element 110 can be uncoupled from the proximal end 46 of the locking element 40 such as by unscrewing, rotating and/or pulling or otherwise disengaging the elongate element 110 from the proximal end 46 of the locking element 40. The coupling of the elongate element 110 and the locking element 40 can be a simple thread form, a bayonet style locking mechanism, pull lock or other interference fit or friction lock mechanism. The adjacent endplates can engage and hold the device in position such that the device can be uncoupled from components of the delivery system. Once uncoupled from the proximal end 46 of the locking device 40, the elongate element 110 and the delivery cannula 105 can be withdrawn along the axis of insertion leaving the device deployed in its expanded configuration within the disc space between the adjacent vertebrae.

The articulating interbody devices described herein can also expand along more than a single dimension. For example, the devices described herein can expand in lordotic, caudal-cephalad height as well as medial laterally such that the combination of dimensional changes in the perimeter of the device is in more than one plane. These devices in their reduced dimension allow for a reduced dimensional introduction via minimally-invasive access and upon expansion can distract the disc space as well as increase the surface area of support by moving the load bearing to surfaces of the vertebral endplate near the denser perimeter.

FIG. 6 and FIGS. 7A-7F illustrate another implementation of an articulating interbody device 610 that can enlarge in two dimensions, for example, caudal-to-cephalad and anterior-to-posterior. The articulating interbody device 610 can include an anterior cage portion 601*a* slideably coupled to a posterior cage portion 601*p*. The anterior cage portion 601*a* can include an upper plate 615*a* and a lower plate 620*a*. Similarly, the posterior cage portion 601*p* can include an upper plate 615*p* and a lower plate 620*p*. The upper plate 615*a* can include one or more fingers 624*a* that slideably interdigitate with one or more fingers 624*p* of the upper plate 615*p*. Similarly, the lower plate 620*a* can include one or more fingers 630*a* that slideably interdigitate with one or more fingers 630*p* of the lower plate 620*p*. Each of the fingers 624*p* of the upper plate 615*p* and each of the fingers 630*p* of the lower plate 620*p* can include an axially-aligned bore configured to receive a pintle 618. Each of the fingers 624*a* of the upper plate 615*a* and each of the fingers 630*a* of the lower plate 620*a* can include an elongate slot 626 configured to receive the pintle 618 extending through the axially-aligned bore of the upper plate 615*p* and lower plate 620*p*. The anterior cage portion 601*a* and posterior cage portion 601*p* can be coupled together via the pintles 618 extending through the bores of the fingers 624*p*, 630*p* and the slots 626 of the fingers 624*a*, 624*p*. This coupling configuration of the anterior cage portion 601*a* and the posterior cage portion 601*p* allow for them to slide relative to each other and enlarge the device 610 in the anterior-posterior direction.

It should be appreciated that the relative sliding expansion of the cage portions 601*a*, 601*p* can be in a lateral direction relative to the spine. As such, use of the anatomical terms "anterior" and "posterior" to refer to the orientation of the cage portions should not be limiting.

When deployed between adjacent vertebrae, the upper plates 615*a*, 615*p* can be in contact with an endplate of the superior, more cephalad vertebra and the lower plates 620*a*, 620*p* can be in contact with an endplate of the inferior, more caudal vertebra. The upper plates 615a, 615p and lower plates 620a, 620p can each have an external surface that is textured for better association of the device 610 with the endplates.

Figure 6:
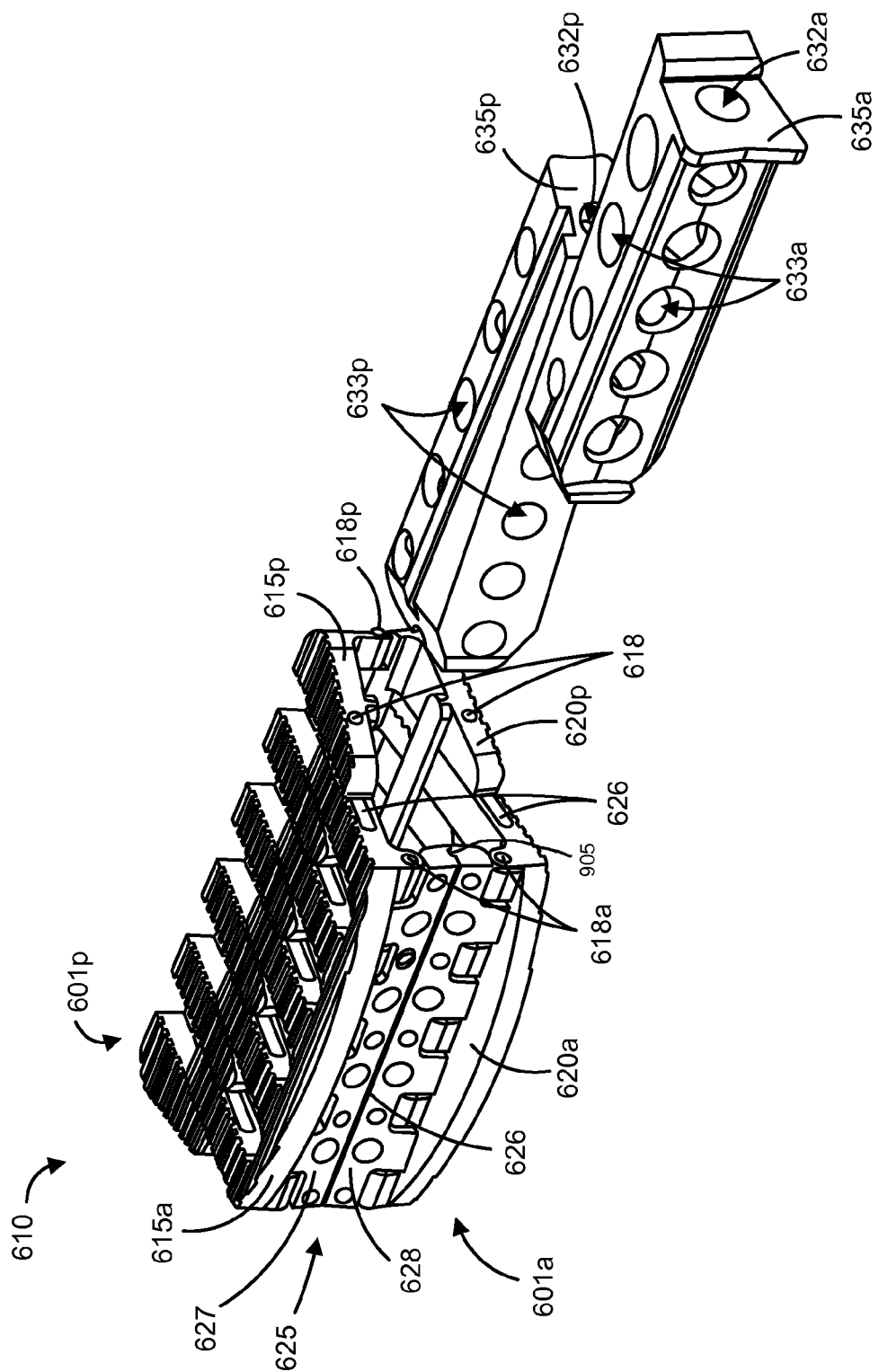
FIG. 6 is a partially exploded view of another implementation of an articulating interbody device, optimized for lateral lumbar surgical approaches (i.e. LLIF procedures)
Figure 7A:
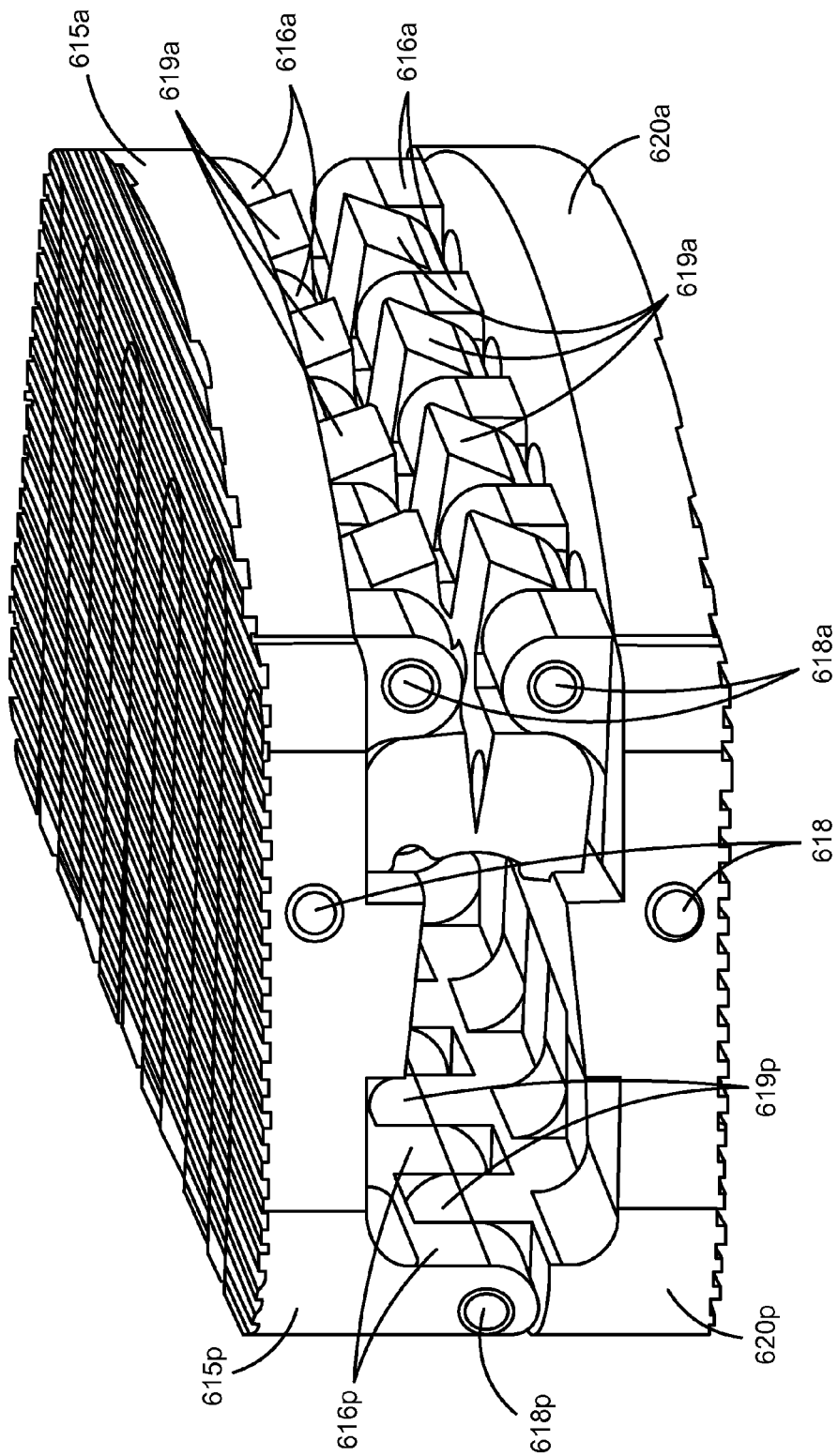
FIG. 7A-7F are perspective views of the deployment of the device in FIG. 6.
Figure 7B:
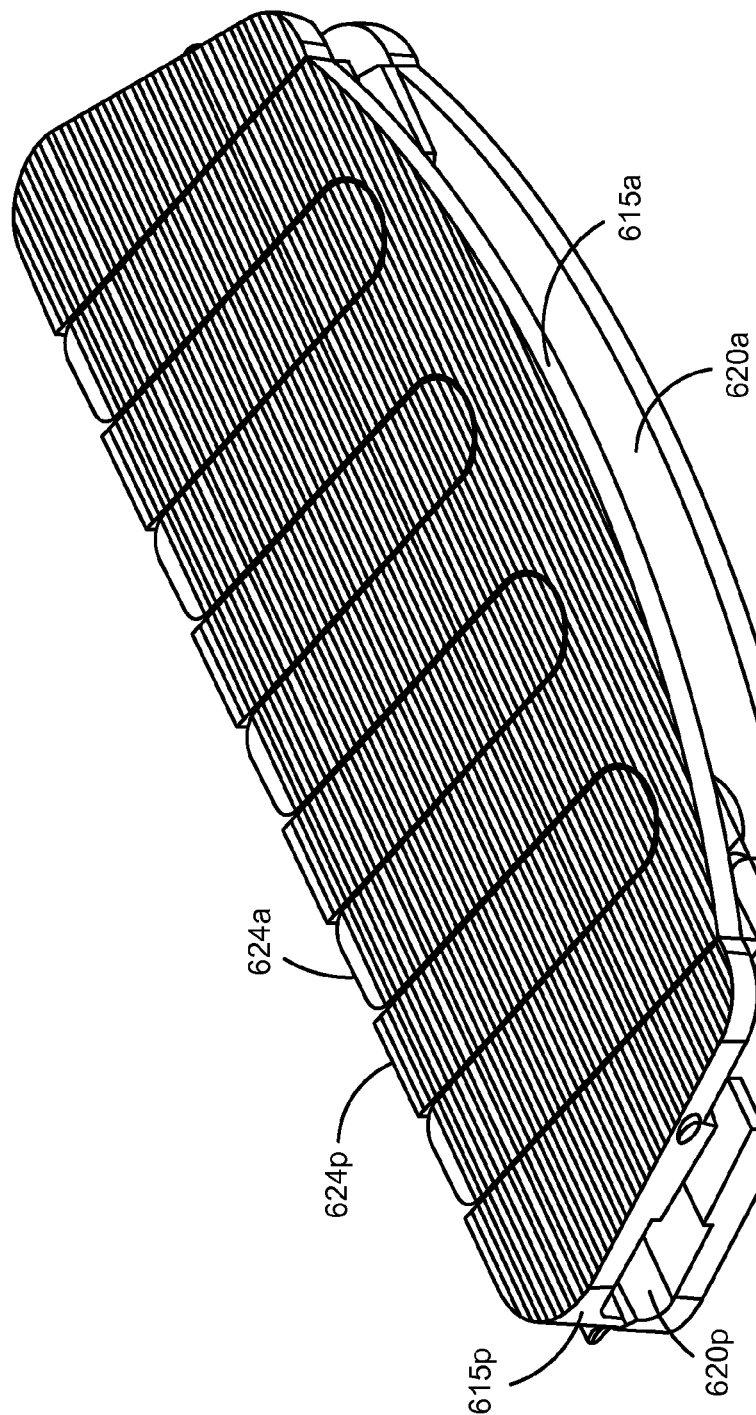
Figure 7C:
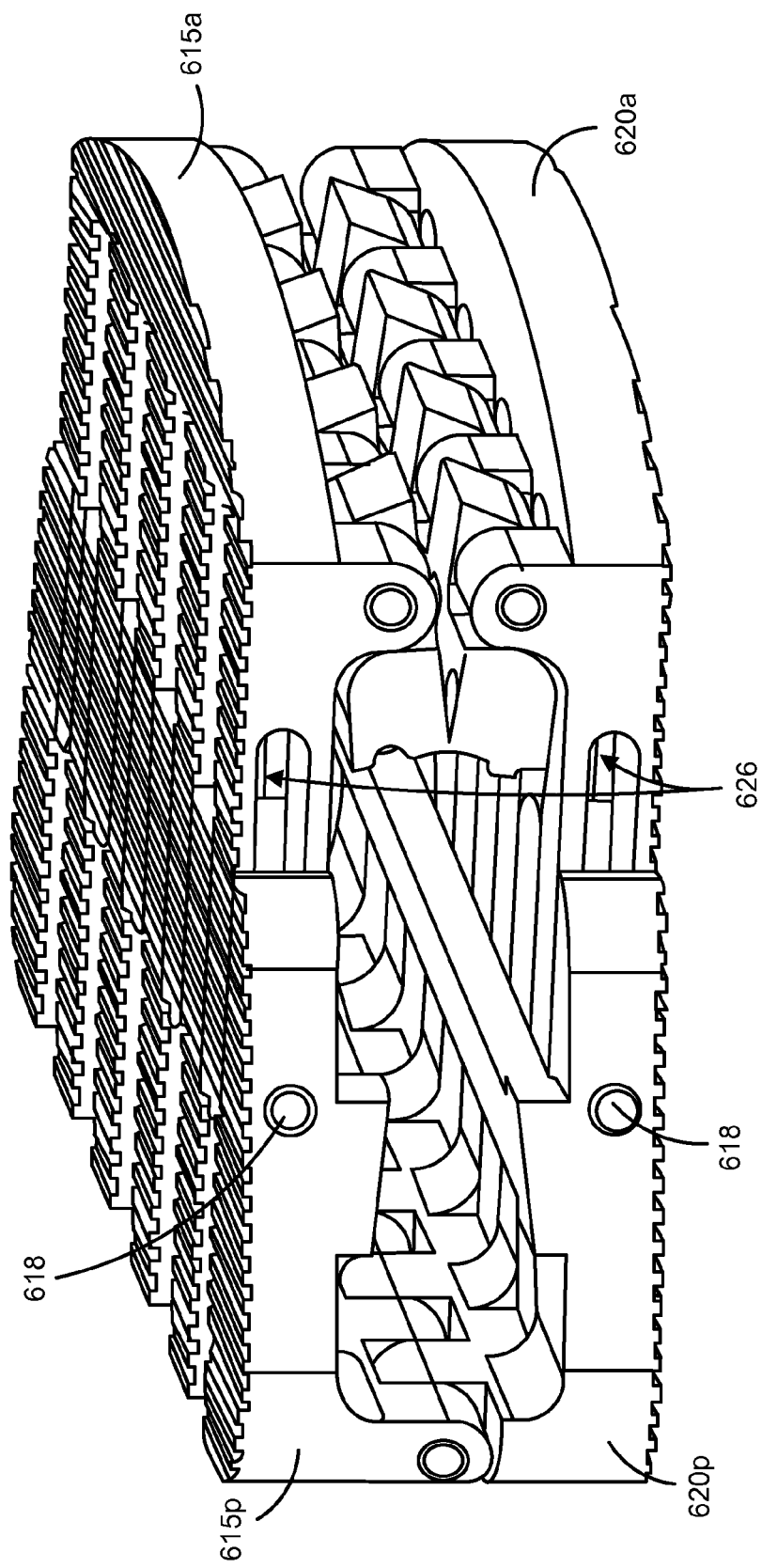
Figure 7D:
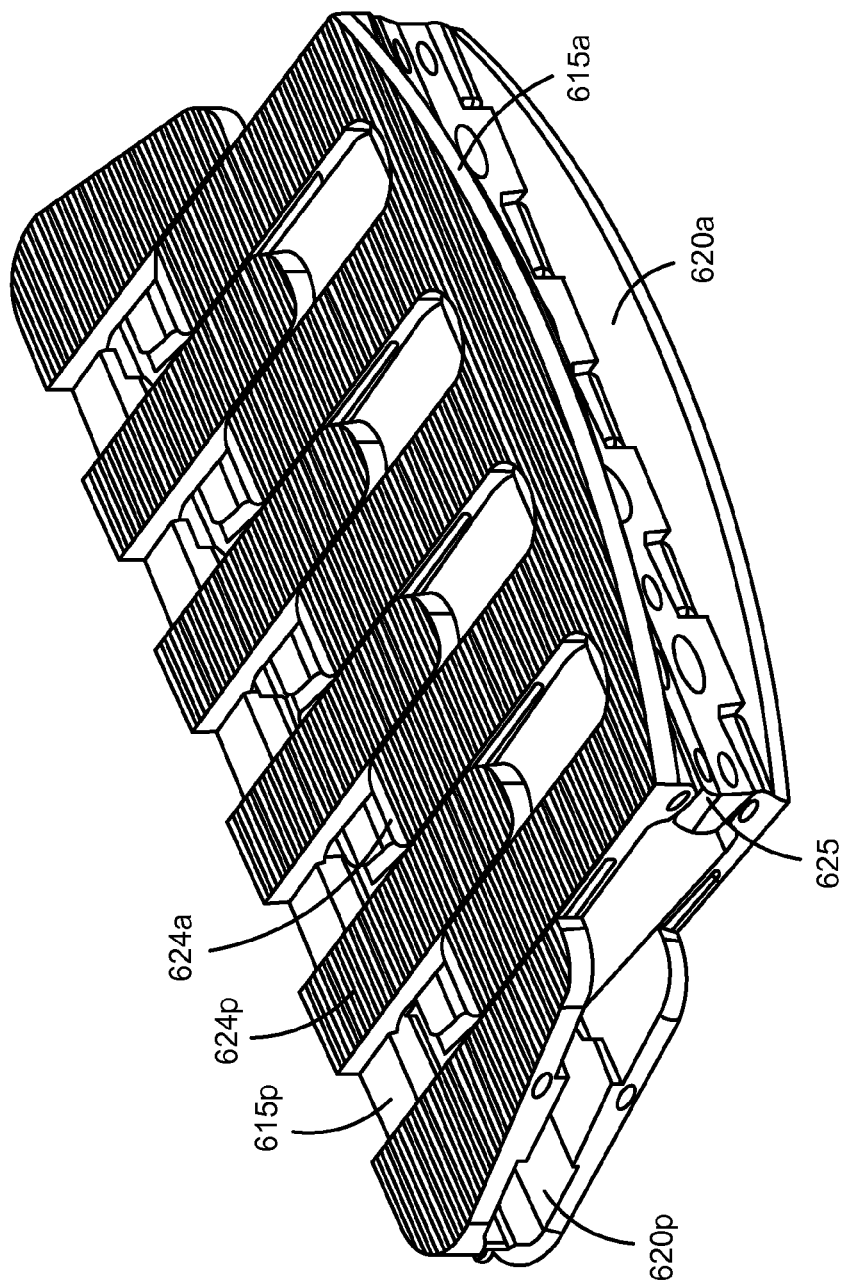
Figure 7E:
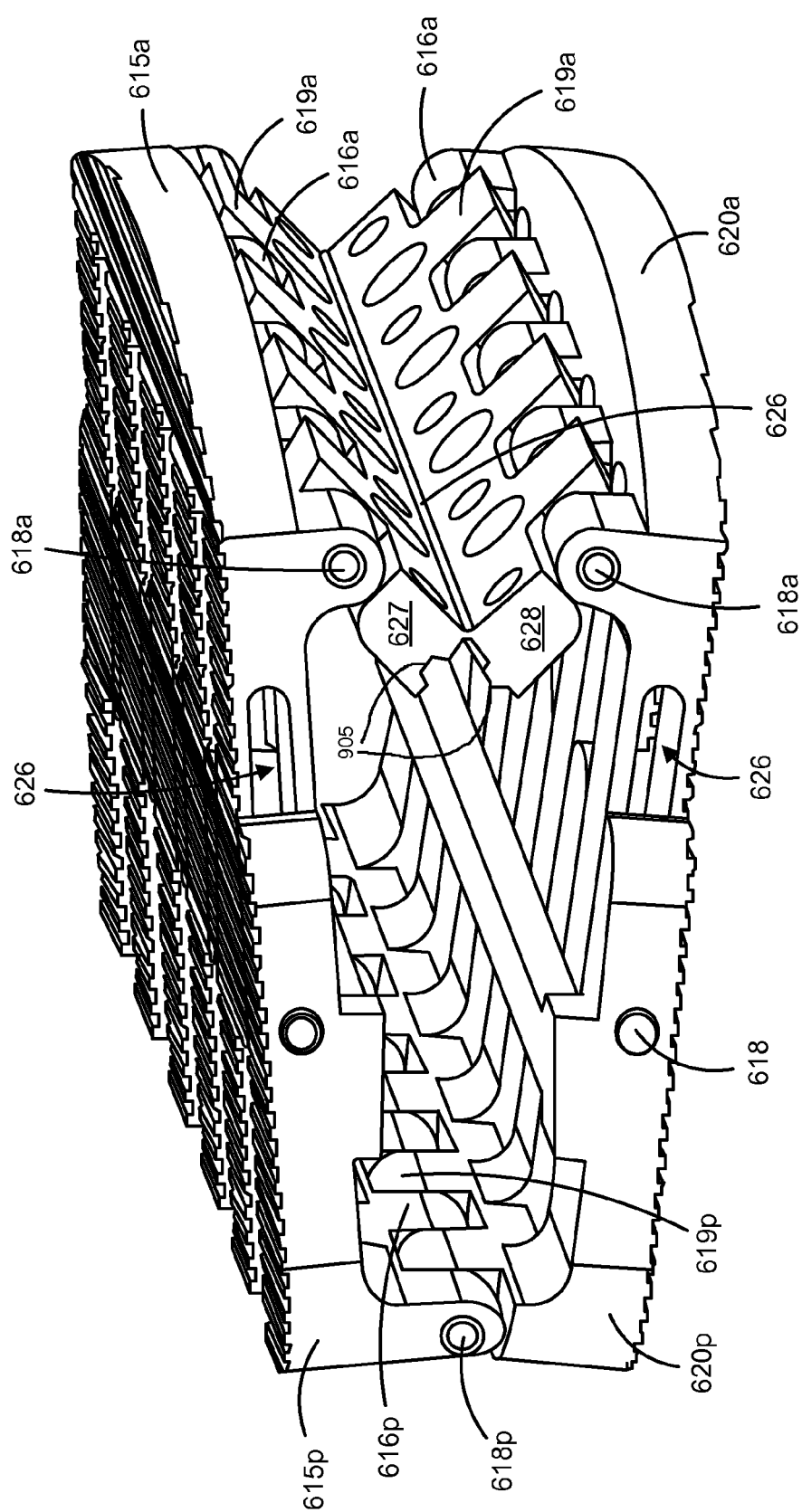
Figure 7F:
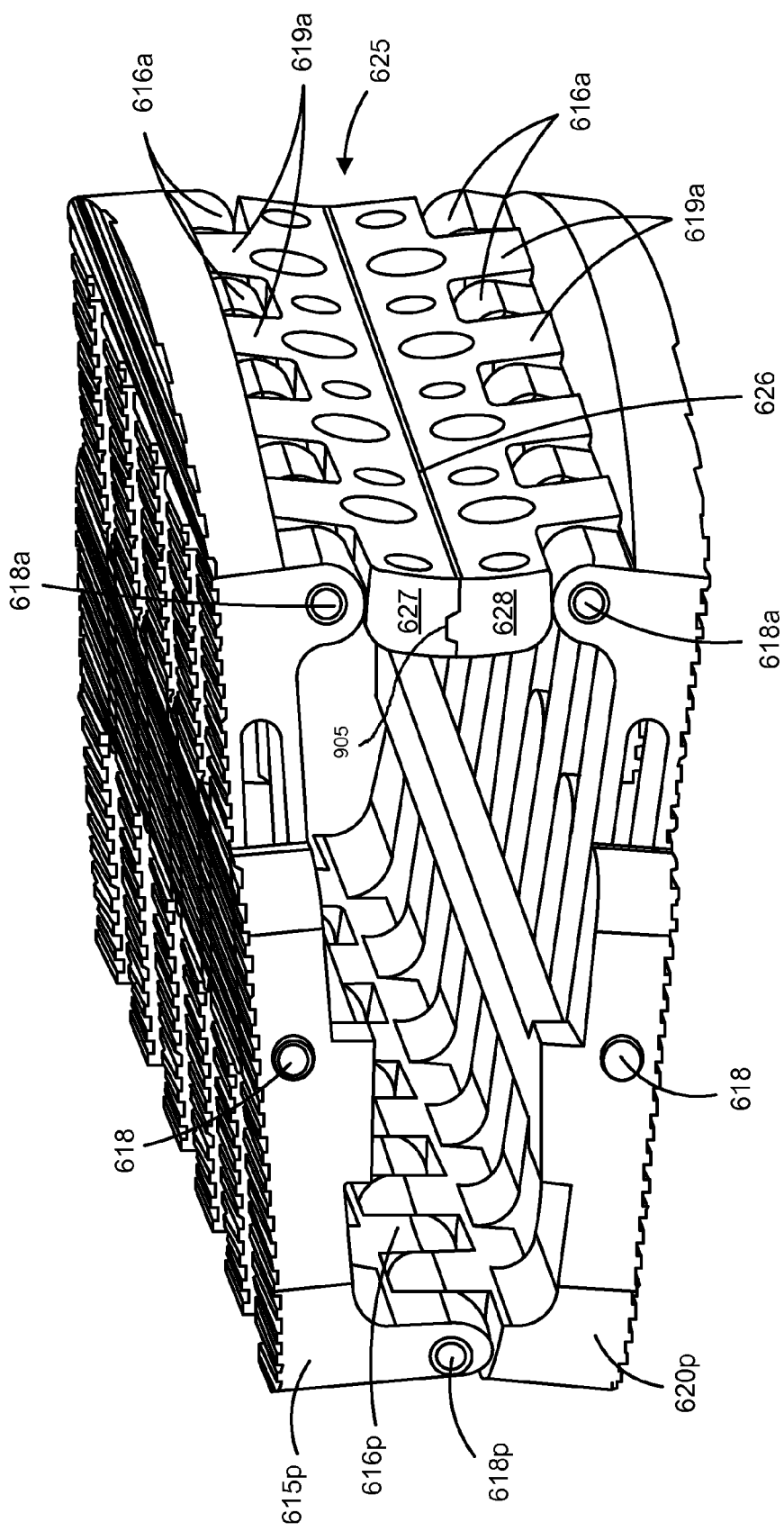

The upper and lower plates 615a, 620a of the anterior cage portion 601a can be rotationally coupled to an articulating sidewall 625 (see FIG. 6). As best shown in FIG. 7A, the upper plate 615a can include a plurality of axially-aligned hinge knuckles 616a on its lateral side that extend downward. Similarly, the lower plate 620a can include a plurality of axially-aligned hinge knuckles 616a on its lateral side that extend upward. The hinge knuckles 616a of the upper plate 615a interdigitate with corresponding upwardly-extending hinge knuckles 619a of the sidewall 625 forming an axially-extending bore. The hinge knuckles 616a of the lower plate 620a interdigitate with corresponding downwardly-extending hinge knuckles 619a of the sidewall 625 forming a second axially-extending bore. The axially-extending bores can receive an axis pin 618a forming a pivot point around which the knuckles 616a, 619a can rotate during expansion (or compression) of the device 610.

Again with respect to FIG. 6, the sidewall 625 can include an upper sidewall portion 627 and a lower sidewall portion 628 connected by a hinge element 626 extending along the length of the sidewall 625. The hinge element 626 can allow for the device 610 to have a reduced dimension appropriate for minimally-invasive insertion and an enlarged dimension such as upon distraction and deployment in the target disc space location. The device 610 can increase in a first dimension such as the caudal-cephalad dimension upon articulating around the hinge element 626. The sidewall hinge element 626 can include an eccentrically positioned "living hinge" or a thin flexure bearing made from the same material as the upper and lower portions 627, 628 of the sidewall 625. The hinge element 626 can allow for the upper and lower sidewall portions 627, 628 to bend or pivot along the line of the hinge element 626 relative to each other with minimal friction, wear or fatigue.

The hinge element 626 can be designed such that the upper and lower sidewall portions 627, 628 are prevented from articulating past a certain rotational position. For example, the hinge element 262 can be prevented from articulating to an on-center or over-center rotational position such that even at maximum device expansion, the sidewall portions 627, 628 are aligned slightly under-center relative to each other and angled towards an internal volume of the device 610. The upper and lower sidewall portions 627, 628 can include corresponding meeting edge surfaces that abut and/or mechanically interlock thereby preventing further pivoting beyond the under-center rotational position. As such, when the device 610 is under compression such as from the superior and inferior vertebrae, the device 610 is biased to collapse inwardly as opposed to outwardly (see FIG. 7F). The meeting edge surfaces can include one or more interlocking elements extending along the meeting edge surface of sidewall portion 627 that mates with one or more corresponding elements extending along the meeting edge surface of the opposing sidewall portion 628 (see FIG. 7E). The interlocking elements can incorporate a variety of interlocking geometries and need not be limited to polygonal as shown in the figure.

Figure 9:
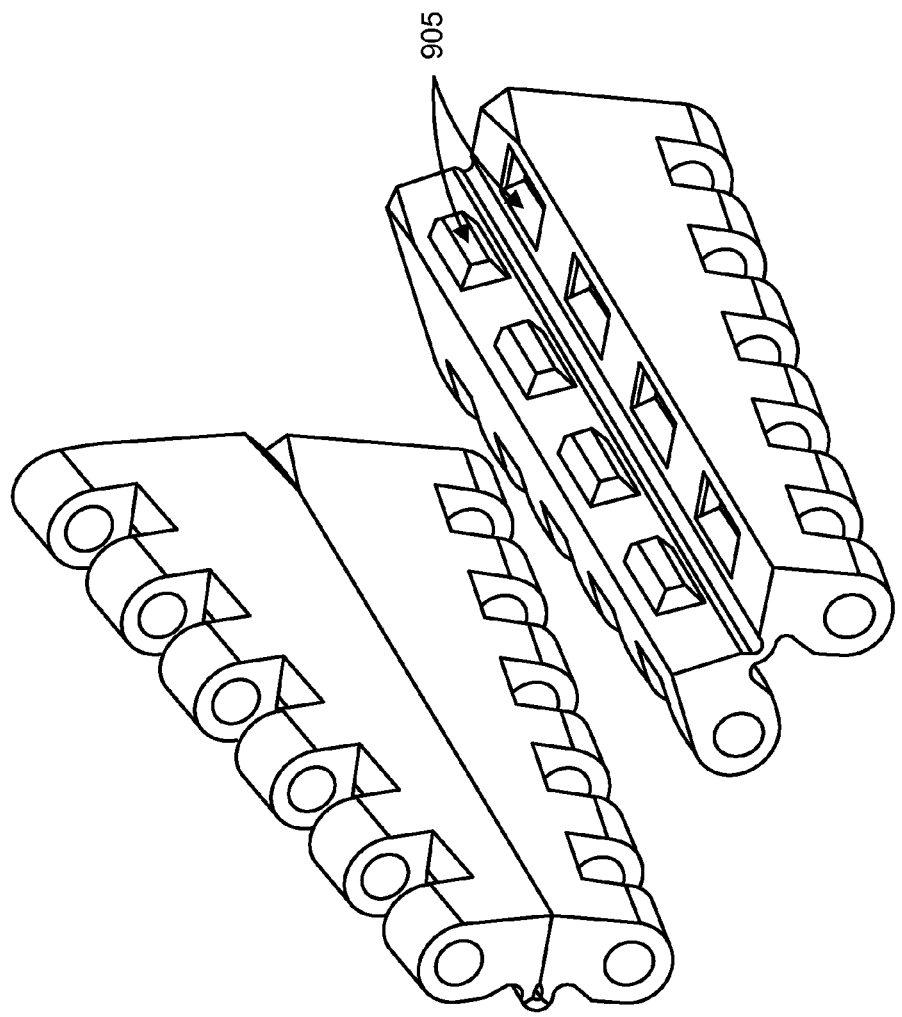
FIG. 9 is a perspective view of an implementation of a hinge stabilizing interlocking element.
Figure 10:
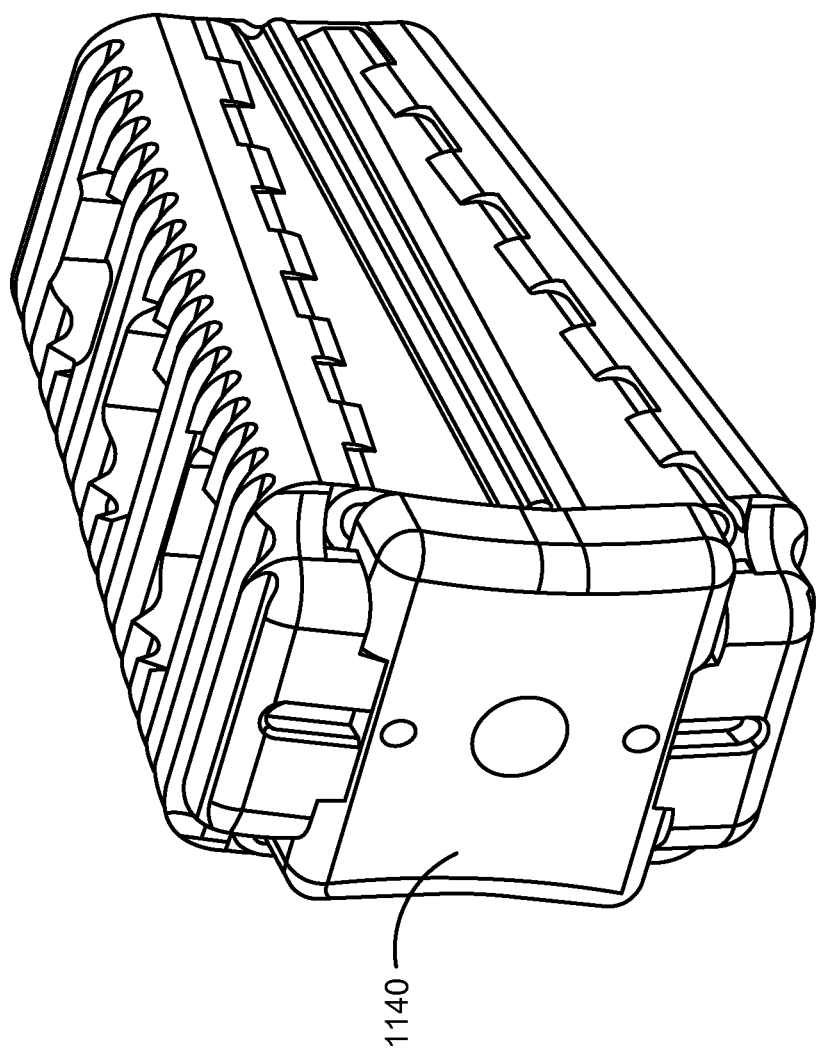
FIG. 10 is a perspective view of an implementation of a device with a distal buttress element having snap lock features.
Figure 11A:
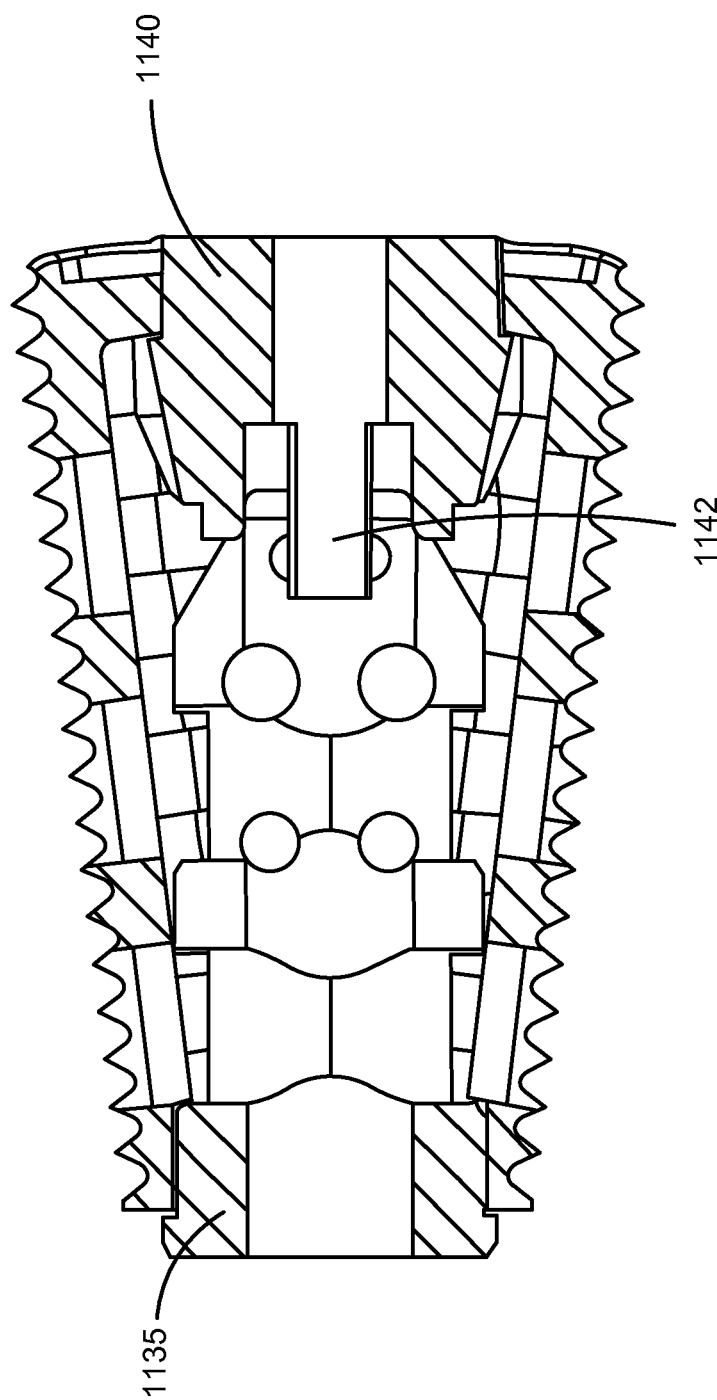
FIG. 11A is a cross-sectional view of the device of FIG. 10 taken along line A-A of FIG. 11B.
Figure 11F:
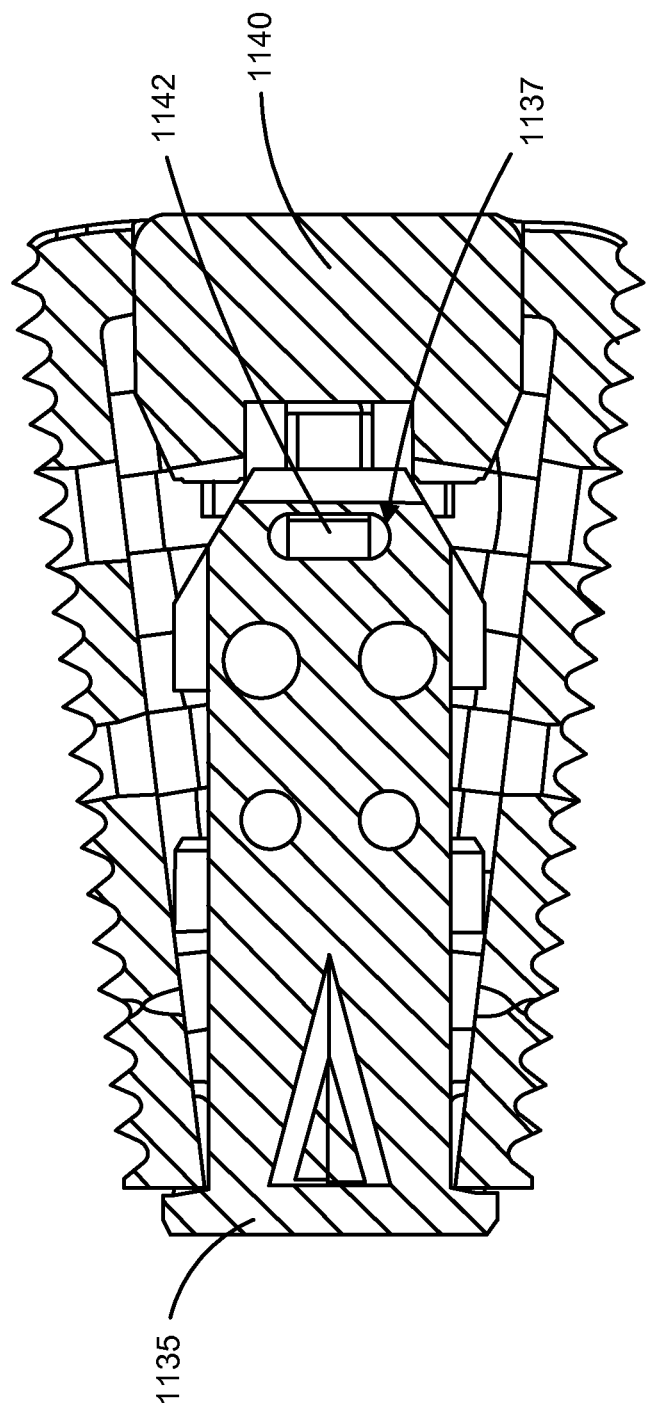
FIG. 11F is a cross-sectional view of the device of FIG. 10 taken along line C-C of FIG. 11B.
Figure 11K:
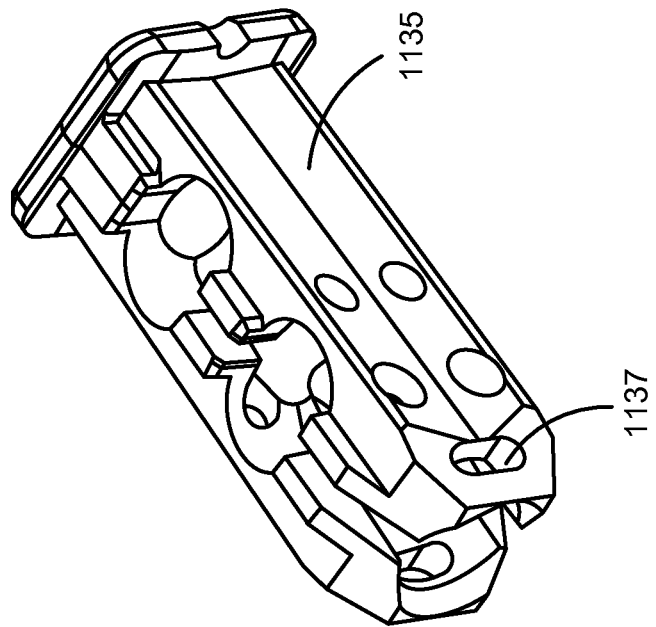
FIG. 11J-11K are perspective views of the buttress and the internal brace, respectively, of the device of FIG. 10.
Figure 11J:
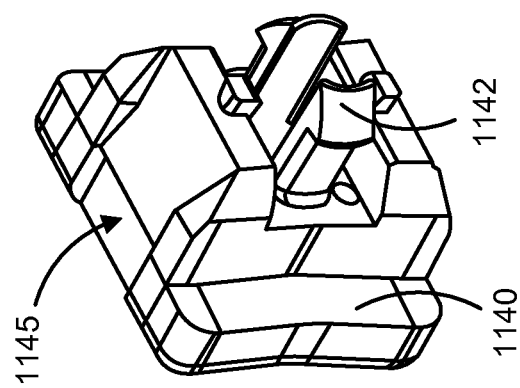
Figure 12A:
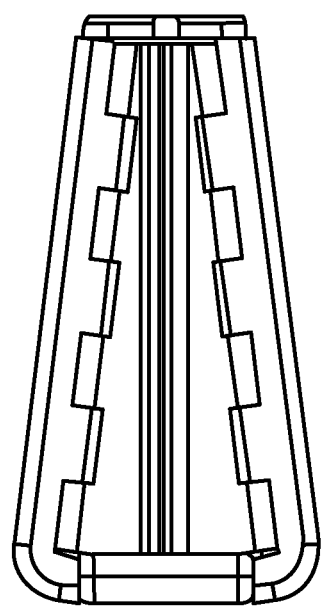
FIG. 12A shows a side view of an implementation of a device configured to undergo expansion in two dimensions following insertion of the internal brace.
Figure 12B:
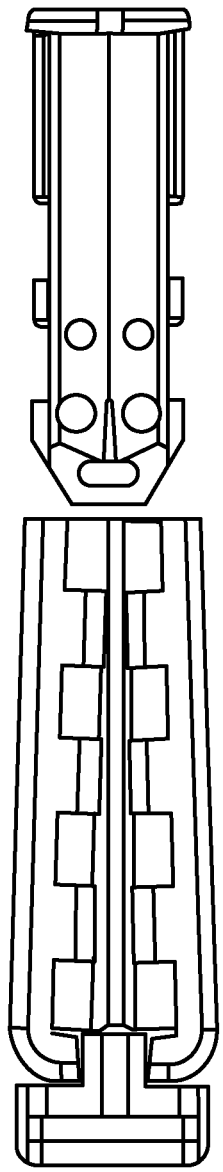
FIG. 12B shows a side view of the device of FIG. 12A prior to insertion of the internal brace.
Figure 12D:
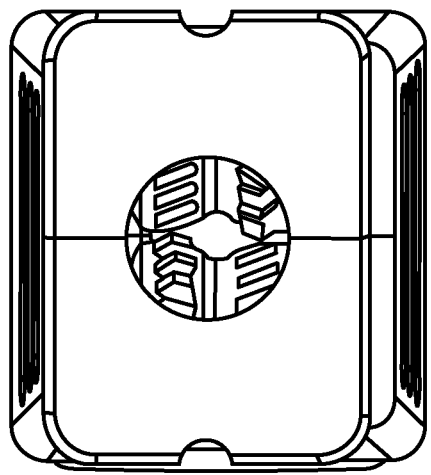
FIG. 12D shows an end view of the device of FIG. 12A prior to expansion.
Figure 12C:
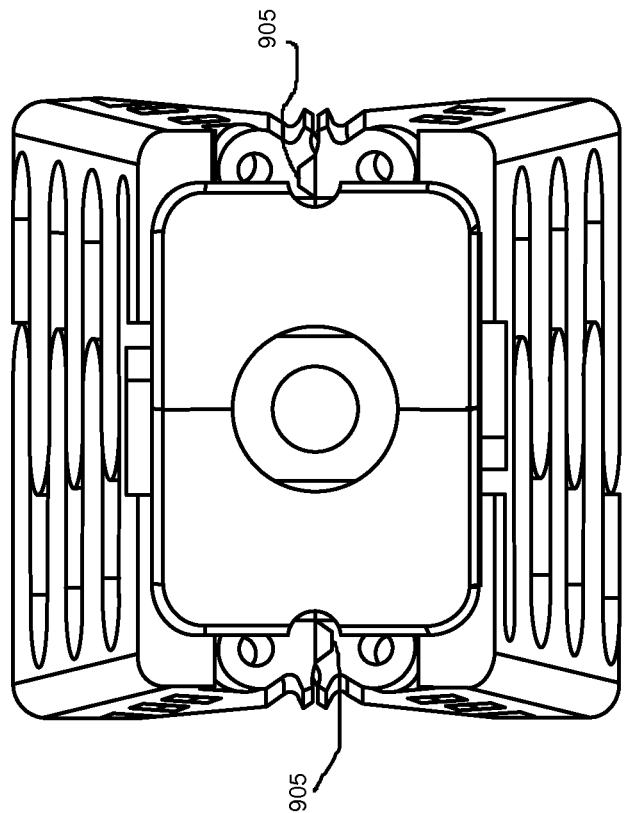
FIG. 12C shows an end view of the device of FIG. 12A following expansion in two dimensions.
Figure 12E:
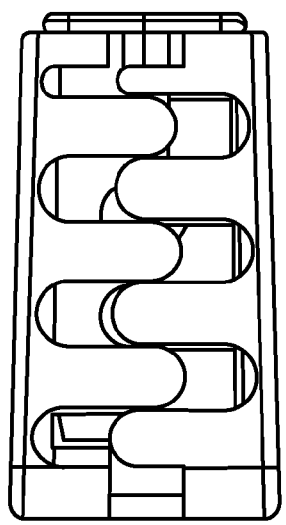
FIG. 12E shows a top-down view of the device of FIG. 12A following expansion.
Figure 12F:
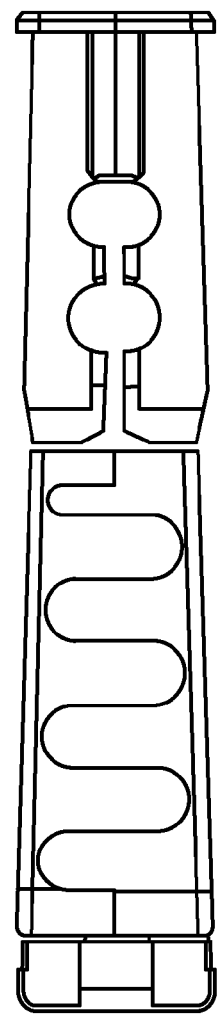
FIG. 12F shows a top-down view of the device of FIG. 12A prior to insertion of the internal brace.
Figure 12H:
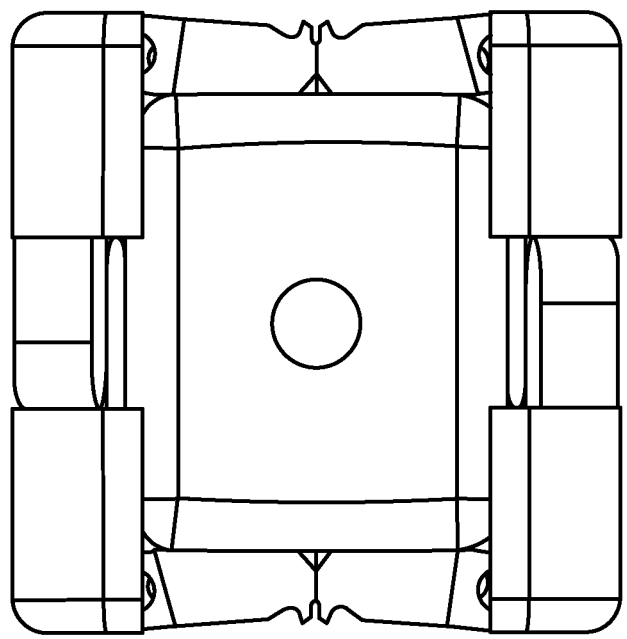
FIG. 12H shows an end view of the device of FIG. 12A following expansion along two dimensions.
Figure 12G:
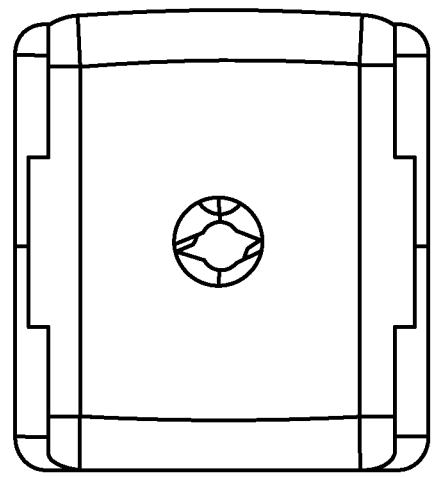
FIG. 12G shows an end view of the device of FIG. 12A prior to expansion.

FIG. 9 shows another implementation of an articulating wall having interlocking elements 905. The one or more interlocking elements 905 can abut, interdigitate, meet and/or interlock upon articulation or deployment of the hinge. The interlocking elements 905 in the deployed state can mitigate shear strain on the living hinge segments of the sidewalls, in a variety of axes. The interlocking elements 905 can present adjacent surface features when the hinge is fully deployed that can abut and/or engage each other to resist translational movement under load in the general axis of compressive load, along all axes within a plane containing the axes of the opposing sidewall hinges, as well as other potentially displacing axes of force. Interlocking elements 905 can be incorporated in any implementation of the devices described herein. For example, interlocking elements can be incorporated in devices as shown in FIGS. 6, 7E, 7F, 12C, and 12D.

The upper and lower plates 615p, 620p of the posterior cage portion 601p can be coupled directly to one another by interdigitating hinge knuckles 616p and 619p coupled by axis pin 618p as shown in FIG. 7A. It should be appreciated that the upper and lower plates 615p, 620p of the posterior cage portion 601p can be coupled to an articulating sidewall 625 as described above with respect to the anterior cage portion 601a. Alternatively, the upper and lower plates 615a, 620a of the anterior cage portion 601a can be coupled directly to one another by interdigitating hinge knuckles 616a and 619a while the upper and lower plates 615p, 620p of the posterior cage portion 601p can be coupled to an articulating sidewall 625. The hinged coupling mechanisms can provide disparate heights between anterior and posterior portions such that a proper lordosis to the region of the spine is achieved upon deployment and expansion of the device 610. For example, if the upper and lower plates 615p, 620p of the posterior cage portion 601p are directly coupled by a hinge therebetween, and the anterior cage portion 601a includes an articulating sidewall 625 coupling the upper and lower plates 615a, 620a, the posterior end of the device 610 can expand to a lesser degree than the anterior end of the device 610 resulting in a taper from anterior extent to posterior extent of the device 610 such that it provides a convexity anteriorly and a concavity posteriorly. It should be appreciated that both portions 601a, 601p can include a sidewall 625 and the sidewalls 625 can have the same dimensions or different dimensions. The disparity in dimensions could still effect a lordotic inclination that is oriented in the proper plane. It should be appreciated that the expansion can occur along an axis or arc other than that associated with caudal-cephalad height expansion (i.e. greater in posterior portion than anterior portion).

As mentioned above, the device 610 can be biased to collapse inwardly upon compressive load on the upper 615a, 615p and lower plates 620a, 620p due to the under-center rotation of the sidewall portions 627, 628 relative to one another. As shown in FIG. 6, one or more internal braces 635 can be positioned within an internal volume of the device 610 to internally support loading between the plates 615a, 615p, 620a, 620p and sidewall 625. A first internal brace 635p can be positioned within the internal volume of the posterior cage portion 601p and a second internal brace 635a can be positioned within the anterior cage portion 601a. As with previous implementations, the leading end of the internal braces 635a, 635p can have a more narrow dimension compared to the trailing end of the internal braces 635a, 635p providing them with a wedge shape. The wedge shape of the internal braces 635a, 635p can be configured to urge the device 610 to pivot around axis pins 618a, 618p into an expanded configuration as the internal braces 635a, 635p are urged distally and inserted into the internal volume of the device 610. The internal braces 635a, 635p can be placed under superior-inferior compression as well as compression from hinged elements and sidewalls.

As with previous implementations, the internal brace 635a, 635p can be deployed using a push-pull mechanism of distraction force. The device 610 can include one or more pliable tethers such as sutures, cable, wires or other element can extend through a portion of the device 610 and out proximally such as through a delivery cannula to be captured by a user or another delivery device element. The tethers can be used to apply a pulling force in a direction opposite the pushing force during insertion of the internal brace(s). Thus, the device 610 can be deployed by applying push and pull forces simultaneously resulting in a net zero force and displacement of the device within the disc space. A posterior internal brace can be positioned within a posterior aspect of the device using such a push-pull deployment mechanism. The posterior internal brace can maintain the device 610 in a distracted or expanded configuration. An anterior internal brace can then be inserted within an anterior aspect of the device 610 to lock the posterior internal brace in its final position. It should be appreciated, however, that a single internal brace can be used as well.

Each of the internal braces 635a, 635p can include a central bore 632a, 632p and a plurality of through-holes 633a, 633p extending from the central bore 632a, 632p through one or more surfaces of the internal brace 635a, 635p. The bore 632a, 632p and through-holes 633a, 633p can allow for the containment and positioning of filler material as described above. The central bore 632a, 632p can have thread forms that can be used during delivery of the device, also as described above.

The interbody device 610 can be delivered from a lateral approach (via transpoas muscle) and can expand in both anterior-posterior direction as well as cephalad-caudal direction. The dimensional expansion of the device 610 can occur in a sequential manner or simultaneously. For example, the device 610 can be initially expanded anterior-posterior by a distraction tool and then expanded caudal-cephalad by the same or a separate distraction tool placed in the internal anterior aspect of the internal volume. A spreading insertional instrument can be used to expand the device in the anterior-posterior directions such that the anterior and posterior cage portions slide relative to one another away from the fully interdigitated configuration.

Figure 8A:
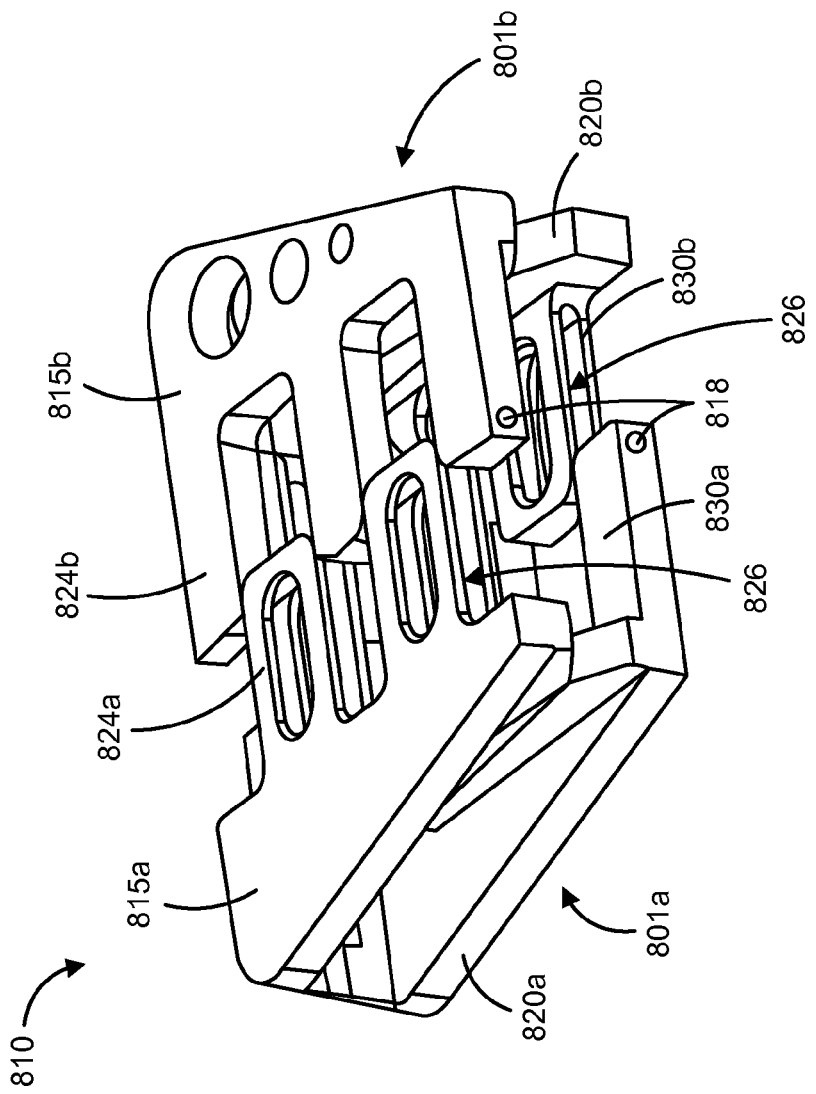
FIG. 8A-8C are various perspective views of another implementation of an articulating interbody device, optimized for anterior lumbar surgical approaches (i.e. ALIF procedures).
Figure 8B:
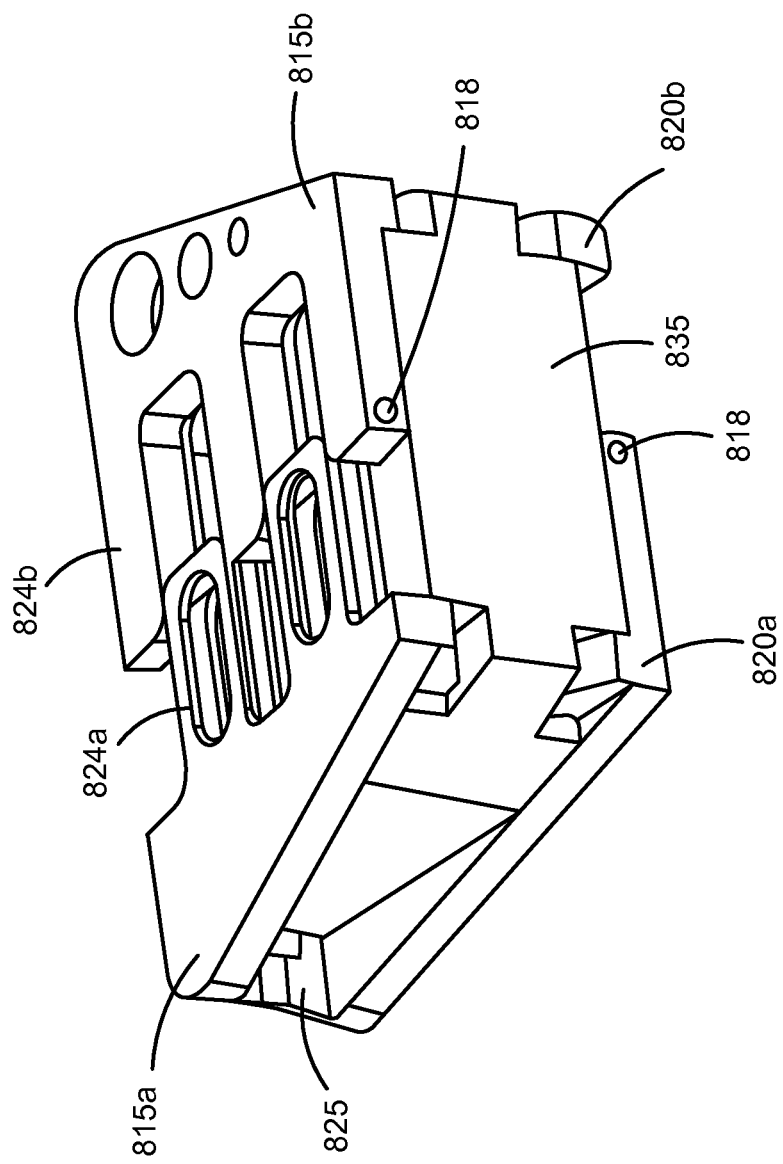
Figure 8C:
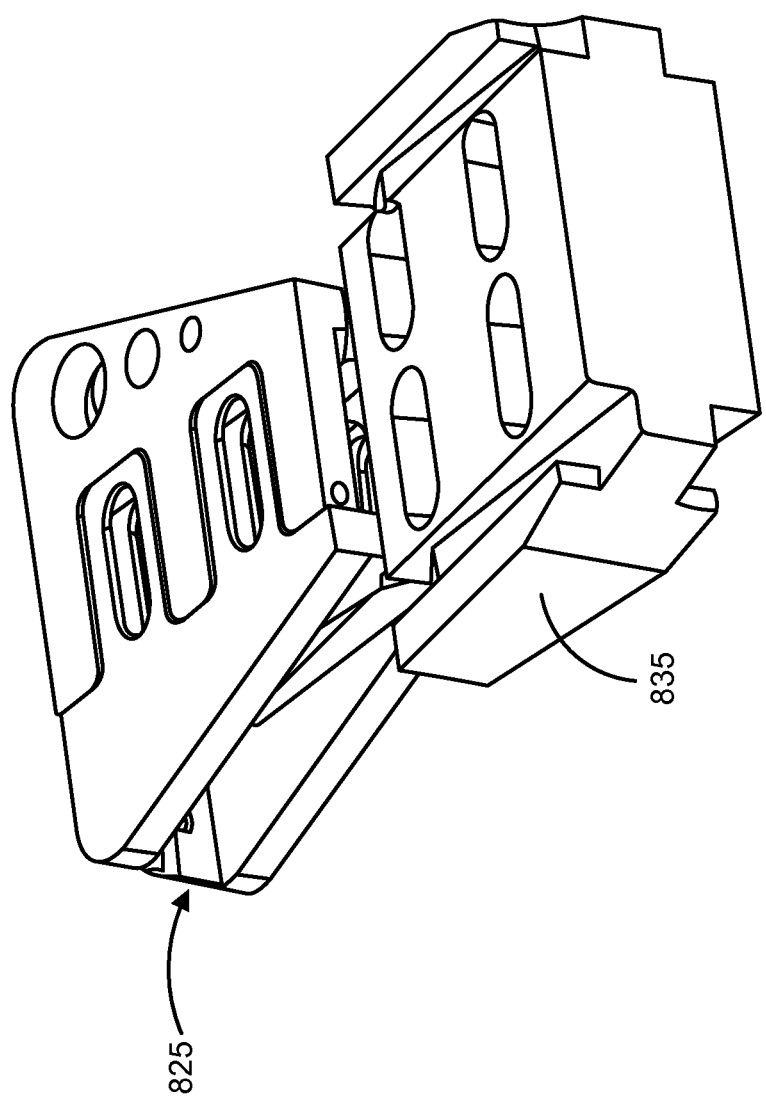

FIGS. 8A-8C and also FIGS. 12A-12H, and 13A-13B illustrate additional implementations of articulating interbody devices that can expand in two dimensions, including lordotic, caudal-to-cephalad expansion as well as generally orthogonal to that axis within the axial plane or medial-laterally. The devices can be particularly useful for performing TLIF procedures.

As shown in FIGS. 8A-8C, the device 810 can include a first cage portion 801a slideably coupled to a second cage portion 801b. The first cage portion 801a can include an upper plate 815a and a lower plate 820a. Similarly, the second cage portion 801b can include an upper plate 815b and a lower plate 820b. The upper plate 815a can include one or more fingers 824a that slideably interdigitate with one or more fingers 824b of the upper plate 815b. Similarly, the lower plate 820a can include one or more fingers 830a that slideably interdigitate with one or more fingers 830b of the lower plate 820b. Each of the fingers 824b of the upper plate 815b and each of the fingers 830a of the lower plate 820a can include an axially-aligned bore configured to receive a pintle 818. Each of the fingers 824a of the upper plate 815a and each of the fingers 830b of the lower plate 820b can include an elongate slot 826 configured to receive the pintle 818. The first cage portion 801a and second cage portion 801b can be coupled together via the pintles 818 extending through the bores of the fingers 824b, 830a and the slots 826 of the fingers 824a, 830b. This coupling configuration of the first cage portion 801a and the second cage portion 801b allow for them to slide relative to each other and enlarge the device 810 laterally.

When deployed between adjacent vertebrae from an anterior approach, the upper plates 815a, 815b can be in contact with an endplate of the superior, more cephalad vertebra and the lower plates 820a, 820b can be in contact with an endplate of the inferior, more caudal vertebra. The upper plates 815a, 815b and lower plates 820a, 820b can each have an external surface that is textured for better association of the device 810 with the endplates. The upper plates 815a, 815b and lower plates 820a, 820b can be coupled to respective articulating sidewalls 825. The sidewalls 825 can include one or more of the hinge element varieties described herein including interdigitating hinge knuckles that rotate around a pintle or a living hinge element. The device 810 can increase in a first dimension such as laterally as well as in the caudal-cephalad dimension upon articulating around a hinge element of the sidewall.

The device 810 can include one or more internal braces 835. The internal brace 835 can be positioned from an anterior approach within an internal volume of the device 810 to internally support loading between the plates 815a, 815b, 820a, 820b and their sidewalls 825. The leading end of the internal brace 835 can have a reduced dimension compared to the trailing end of the internal brace 835 providing the brace with a wedge shape to achieve proper lordosis to the disc space. Insertion of the internal brace 835 through the internal volume of the device 810 can cause the device 810 to expand in a caudal-cephalad dimension as well as laterally. As with previous implementations, the internal brace 635a, 635p can be deployed using a push-pull mechanism of distraction force.

The devices described here can also include one or more expansion stop elements that limit expansion preventing overexpansion of one or more articulating elements. In one implementation as shown in FIGS. 13A and 13B, the upper plate and the lower plate can each have one or more fingers 1324a, 1324b that slideably interdigitate with one another. One or more of fingers 1324a can have a stop element 1305a projecting from an end. Similarly, one or more of fingers 1324b can have a stop element 1305b projection from an end. As fingers 1324a, 1324b slide relative to one another, for example in a medial-lateral direction, to enlarge the device in the axial direction, the limit elements 1305a, 1305b on the juxtaposed fingers 1324a, 1324b can abut one another and block the fingers 1324a, 1324b from translating further relative to one another (see FIG. 13B). These stop elements 1305a, 1305b can prevent overexpansion of the device beyond the intended limit. It should be appreciated that although the stop elements are shown preventing overexpansion along the axial direction that other configurations are considered herein to prevent overexpansion along other translation directions.

One or more implementations of the devices described herein can include one or more features that improve connections between the components to improve resistive stability (see FIGS. 10 and FIGS. 11A-11K). For example, the internal brace 1135 and/or the anterior buttress 1140 of the devices described herein can include one or more snap locking features. The upper and lower surfaces of the anterior buttress 1140 can include a feature 1145 that can engage with a corresponding feature on the upper and lower plates of the expanded device (see FIG. 11J). Further, snap locking between the anterior buttress 1140 and the internal brace 1135 can occur with distal advancement of the internal brace 1135 within the extended walls and upper and lower plates. The snap locking can occur as a result of mating features 1142 on the proximal or posterior aspect of the buttress 1140 that marry with corresponding mating features 1137 on the distal or anterior aspect of the internal brace 1135 (see FIGS. 11F and 11K).

Both the buttress 1140 and the internal brace 1135 can be configured to substantially recede to a prescribed depth respectively, within the distal and proximal aspects of the internal void of the expanded cage. The depths of recession and procession of the respective buttress 1140 and internal brace 1135 can be stopped by flanged surfaces that abut the anterior and posterior surfaces of the upper and lower plates along with respective edges of the sidewalls. The portions of the buttress 1140 and the internal brace 1135 that fill and support the side walls and the upper and lower plates, provides substantial load bearing support. This assembled and integrative component design confers exceptional compressive load bearing capacity and greatly enhances resistive stability to torsional loads imparted relative to the long axis (from proximal to distal) of the cage in its deployed configuration.

The interbody devices described herein can be used for a variety of surgical applications in which an interosseous space exists. The devices can be delivered in an initially collapsed or approximated condition such that therapeutic intervention includes distracting the interosseous space with subsequent stabilization (e.g. a degenerative intervertebral disc space). The interbody devices described herein can be deployed into evacuated intervertebral disc spaces, for example, following removal of disc material and excoriation of the endplates. Another potential application for the devices described herein is for the treatment of an existing or created bone defect, such as might occur in a bone cyst or reduced fracture. This application as well as others can be deployed via percutaneous methods via a delivery cannula (s). Various methods and devices can be used to provide access to the disc space to be treated. The disc space can be a prepared disc space such as a partially-vacated disc space. Access pathways can be formed pursuant to methods and devices described in, for example, U.S. Patent Application Publication Nos. 2007-0162044, 2009-0312764, and 2011-0009869, which are each incorporated by reference herein in their entirety. It should be appreciated that the pathways can be formed such that the devices can be inserted via an anterior, posterior and/or lateral approach.

The interbody devices described herein can be constructed of biocompatible materials including platinum, gold, palladium, rhenium, tantalum, tungsten, molybdenum, nickel, cobalt, stainless steel, memory-shaped alloys (e.g. Nitinol, titanium/nickel alloy, Nitinol wire mesh) with or without radiolucent material (e.g. PEEK, Victrex Corp. PolyEtherEtherKetone, or other polymer material). Use of both radiodense and radiolucent elements within the interbody devices can provide enhanced mechanical performance while affording improved radiologic monitoring of interosseous bone healing.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A device comprising:
   a caudal plate configured to be positioned adjacent a first vertebral endplate within an intervertebral disc space;
   a cephalad plate configured to be positioned adjacent a second vertebral endplate within the intervertebral disc space;
   at least one sidewall rotatably coupled to both the caudal and cephalad plates, wherein the at least one sidewall having an upper sidewall portion having a first meeting edge surface coupled by a hinge element to a second meeting edge surface of a lower sidewall portion,
   wherein when in a low profile configuration the hinge element folds inward, and when fully expanded in at least a first dimension to a high profile configuration, the hinge element is restricted from achieving an on-center and an over-center rotational position around the hinge element such that the device is biased to collapse inwardly upon compression loading; and
   wherein when the device is in the high-profile configuration the upper sidewall portion and the lower sidewall portion are aligned under-center relative to each other and angled towards an interval volume, and the first meeting edge surface abuts the second meeting edge surface thereby preventing further pivoting of the hinge element beyond an under-center rotational position.

2. The device of claim 1, further comprising at least one brace element configured to be positioned within the confines of the caudal and cephalad plates and the at least one sidewall of the device, wherein the at least one brace element resists compressive loading of the device along an axis or axes extending between the caudal and cephalad plates via the restriction of at least one sidewall's under-center rotated hinge element from displacing toward the interior of the device.

3. The device of claim 2, wherein the at least one brace element comprises at least one contiguous osteoconductive channel extending from a caudal surface of the brace element to a cephalad surface of the brace element.

4. The device of claim 2, further comprising a buttress element having an upper surface coupled to the caudal plate and a lower surface coupled to the cephalad plate, wherein one or more apertures extend through the buttress element.

5. The device of claim 4, further comprising one or more pliable tethers extending through the one or more apertures in the buttress element.

6. The device of claim 5, wherein the one or more pliable tethers are configured to apply a pulling force on the device in a direction away from the anterior buttress as a pushing force is applied on the at least one brace element in a direction towards the anterior buttress to maintain a net zero force on the device during insertion of the at least one brace element within the confines of the caudal and cephalad plates.

7. The device of claim 6, wherein the net zero force prevents migration of the device between the first and second vertebral endplates during expansion of the device with the at least one brace element.

8. The device of claim 2, wherein the device enlarges in a second dimension.

9. The device of claim 8, wherein the first dimension comprises a caudal-to-cephalad dimension and the second dimension comprises medial-lateral dimension or an anterior-to-posterior dimension.

10. The device of claim 8, wherein the caudal and cephalad plates each comprises a first portion slideably coupled to a second portion.

11. The device of claim 10, wherein the first portions and second portions each comprises one or more fingers slideably interdigitated with one another.

12. The device of claim 11, wherein each of the one or more fingers further comprises a stop element configured to abut one another upon sliding translation to prevent overexpansion along the second dimension.

13. The device of claim 1, wherein at least one of the caudal plate, the cephalad plate, and the at least one sidewall are radiolucent.

14. The device of claim 1, wherein osteoinductive, osteoproliferative, and/or osteoconductive material extends from the first vertebral endplate to the second vertebral endplate.

15. The device of claim 1, wherein at least one of the caudal plate and the cephalad plate has a textured external surface.

16. The device of claim 1, wherein the first dimension is along an axis or arc other than a caudal-cephalad dimension.

17. The device of claim 1, wherein the first meeting edge surface has at least a first interlocking element configured to abut with at least one corresponding second interlocking element positioned on the second meeting edge surface when the device is in the higher-profile configuration.

18. The device of claim 17, wherein the first and second interlocking elements resist translational movement of the upper sidewall portion relative to the lower sidewall portion due to application of a compressive load or shear loading of the at least one sidewall when the device is fully dimensionally expanded and under compression between the first and second vertebral endplates.

19. The device of claim 1, further comprising an anterior buttress comprising a surface having a snap lock feature that engages one or both of the caudal and cephalad plates.

20. The device of claim 19, wherein the at least one brace element further comprises a surface having a snap lock feature that engages the snap lock feature of the anterior buttress.

21. The device of claim 1, wherein the at least one sidewall is constructed of a radiolucent material, wherein the radiolucent material is a polymer material.

22. The device of claim 21, wherein the hinge element comprises a thin flexure bearing made from the polymer material allowing the upper and lower sidewall portions to bend or pivot along a line of the hinge element relative to each other.

23. A device comprising:
a caudal plate configured to be positioned adjacent a first vertebral endplate within an intervertebral disc space;
a cephalad plate configured to be positioned adjacent a second vertebral endplate within the intervertebral disc space;
at least one sidewall rotatably coupled to both the caudal and cephalad plates, wherein the at least one sidewall having an upper sidewall portion having a first meeting edge surface coupled by a hinge element to a second meeting edge surface of a lower sidewall portion; and
at least one brace element configured to be positioned within an interior of the device between the caudal and cephalad plates and the at least one sidewall of the device,
wherein when in a low profile configuration the hinge element folds inward, and when expanded to a higher-profile configuration, the hinge element is restricted from achieving an on-center or over-center rotational position around the hinge element upon dimensional expansion of the device in at least a first dimension such that the device is biased to collapse inwardly upon compression loading;
wherein the upper sidewall portion and the lower sidewall portion are aligned under-center relative to each other and angled towards an interval volume, and the first meeting edge surface abuts the second meeting edge surface thereby preventing further pivoting of the hinge element beyond an under-center rotational position; and
wherein the at least one brace element resists compressive loading of the device along an axis or axes extending between the caudal and cephalad plates via the restriction of at least one sidewall's under-center rotated hinge element from displacing toward the interior of the device.

24. A device comprising:
a caudal plate configured to be positioned adjacent a first vertebral endplate within an intervertebral disc space;
a cephalad plate configured to be positioned adjacent a second vertebral endplate within the intervertebral disc space;
at least one sidewall rotatably coupled to both the caudal and cephalad plates, wherein the at least one sidewall has an upper sidewall portion having a first meeting edge surface coupled by a hinge element to a second meeting edge surface of a lower sidewall portion,
wherein when in a low profile configuration the hinge element folds inward, and when expanded to a higher-profile configuration, the hinge element is restricted from achieving an on-center or over-center rotational position around the hinge element upon dimensional expansion of the device in at least a first dimension such that the device is biased to collapse inwardly upon compression loading;
wherein the upper sidewall portion and the lower sidewall portion are aligned under-center relative to each other and angled towards an interval volume, and the first meeting edge surface abuts the second meeting edge surface thereby preventing further pivoting of the hinge element beyond an under-center rotational position;
wherein the first meeting edge surface has at least a first interlocking element configured to abut with at least one corresponding second interlocking element positioned on the second meeting edge surface when the device is in the higher-profile configuration; and
wherein the first and second interlocking elements resist translational movement of the upper sidewall portion relative to the lower sidewall portion due to application of a compressive load or shear loading of the at least one sidewall when the device is fully dimensionally expanded and under compression between the first and second vertebral endplates.

25. A device comprising:
a caudal plate configured to be positioned adjacent a first vertebral endplate within an intervertebral disc space;
a cephalad plate configured to be positioned adjacent a second vertebral endplate within the intervertebral disc space;
at least one sidewall rotatably coupled to both the caudal and cephalad plates, wherein the at least one sidewall having an upper sidewall portion having a first meeting edge surface coupled by a hinge element to a second meeting edge surface of a lower sidewall portion; and
an anterior buttress comprising a surface having a snap lock feature that engages one or both of the caudal and cephalad plates,
wherein when in a low profile configuration the hinge element folds inward, and when expanded to a higher-profile configuration, the hinge element is restricted from achieving an on-enter or over-center rotational position around the hinge element upon dimensional expansion of the device in at least a first dimension such that the device is biased to collapse inwardly upon compression loading; and
wherein the upper sidewall portion and the lower sidewall portion are aligned under-center relative to each other and angled towards an interval volume, and the first meeting edge surface abuts the second meeting edge surface thereby preventing further pivoting of the hinge element beyond an under-center rotational position.

26. A device comprising:
a caudal plate configured to be positioned adjacent a first vertebral endplate within an intervertebral disc space;
a cephalad plate configured to be positioned adjacent a second vertebral endplate within the intervertebral disc space; and
at least one sidewall rotatably coupled to both the caudal and cephalad plates, wherein the at least one sidewall having an upper sidewall portion having a first meeting edge surface coupled by a hinge element to a second meeting edge surface of a lower sidewall portion,
wherein the at least one sidewall is constructed of a radiolucent polymer material and the hinge element comprises a thin flexure bearing made from the polymer material allowing the upper and lower sidewall portions to bend or pivot along a line of the hinge element relative to each other,
wherein when in a low profile configuration the hinge element folds inward, and when expanded to a higher-profile configuration, the hinge element is restricted from achieving an on-center or over-center rotational position around the hinge element upon dimensional expansion of the device in at least a first dimension such that the device is biased to collapse inwardly upon compression loading; and
wherein the upper sidewall portion and the lower sidewall portion are aligned under-center relative to each other and angled towards an interval volume, and the first meeting edge surface abuts the second meeting edge surface thereby preventing further pivoting of the hinge element beyond an under-center rotational position.

* * * * *